(12) United States Patent
Pease et al.

(10) Patent No.: US 7,052,694 B2
(45) Date of Patent: May 30, 2006

(54) DENDRITIC CELL POTENTIATION

(75) Inventors: Larry R. Pease, Rochester, MN (US); Moses Rodriguez, Rochester, MN (US); Daren Ure, Rochester, MN (US); Loc T. Nguyen, Rochester, MN (US); Suresh Radhakrishnan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 135 days.

(21) Appl. No.: 10/196,601

(22) Filed: Jul. 16, 2002

(65) Prior Publication Data
US 2004/0014207 A1 Jan. 22, 2004

(51) Int. Cl.
*A61K 39/395* (2006.01)
*C07K 16/28* (2006.01)

(52) U.S. Cl. .............................. 424/172.1; 530/388.15; 530/388.2; 530/388.22; 530/388.7; 530/388.73; 530/389.1; 530/389.6; 424/143.1; 424/144.1; 424/142.1; 424/152.1; 424/153.1; 424/173.1; 424/278.1; 424/93.1; 424/93.7

(58) Field of Classification Search ............. 530/388.7, 530/388.2, 388.22, 388.15, 388.73, 389.1, 530/389.6; 424/143.1, 144.1, 152.1, 153.1, 424/172.1, 173.1, 278.1, 93.1, 142.1, 93.7
See application file for complete search history.

(56) References Cited

U.S. PATENT DOCUMENTS

2002/0160000 A1* 10/2002 Wood et al. ............. 424/144.1
2002/0164600 A1* 11/2002 Freeman et al. ................ 435/6
2003/0044768 A1* 3/2003 Wood et al. .................... 435/4
2003/0185827 A1* 10/2003 Rodriguez et al. ....... 424/146.1

FOREIGN PATENT DOCUMENTS

WO WO 01/83750 11/2001

OTHER PUBLICATIONS

Aloisi et al., "Relative efficiency of microglia, astrocytes, dendritic cells and B cells in naive CD4+ T cell priming and Th1/Th2 cell restimulation," *Eur. J. Immunol.*, 1999, 29:2705-2714.
Anjuère et al., "Definition of Dendritic Cell Subpopulations Present in the Spleen, Peyer's Patches, Lymph Nodes, and Skin of the Mouse," *Blood*, 1999, 93(2):590-598.
Asakura et al., "Targeting of IgMκ Antibodies to Oligodendrocytes Promotes CNS Remyelination," *J. Neuroscience*, 1998, 18(19):7700-7708.
Banchereau and Steinman, "Dendritic cells and the control of immunity," *Nature*, 1998, 392:245-252.

Banchereau et al., "Immunology of Dendritic Cells," *Annu. Rev. Immunol.*, 2000, 18:767-811.
Bieber et al., "Humoral autoimmunity as a mediator of CNS repair," *Trends in Neurosci.*, 2001, 24(11):S39-S44.
Block et al., "Monomeric Class I Molecules Mediate TCR/CD3ϵ/CD8 Interaction on the Surface of T Cells," *J. Immunol.*, 2001, 167:821-826.
Caux et al., "CD34+ Hematopoietic Progenitors from Human Cord Blood Differentiate Along Two Independent Dendritic Cell Pathways in Response to GM-CSF+ TNFα," *J. Exp. Med.*, 1996, 184:695-706.
Chen et al., "Tumor Immunogenicity Determines the Effect of B7 Costimulation on T Cell-mediated Tumor Immunity," *J. Exp. Med.*, 1994, 179:523-532.
Ciric et al., "Clonal evolution in Waldenstrom macroglobulinemia highlights functional role of B-cell receptor," *Blood*, 2001, 97:321-323.
Cole et al., "The EBV-Hybridoma Technique and Its Application to Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Critchfield et al., "T Cell Deletion in High Antigen Dose Therapy of Autoimmune Encephalomyelitis," *Science*, 1994, 263:1139-1143.
Earnshaw et al., "Mammalian Caspases: Structure, Activation, Substrates, and Functions During Apoptosis," *Annu. Rev. Biochem.*, 1999, 68:383-424.
Fagnoni et al., "Role of B70/B7-2 in CD4+ T-cell immune responses induced by dendritic cells," *Immunology*, 1995, 85:467-474.
Fong and Engleman, "Dendritic Cells in Cancer Immunotherapy," *Annu. Rev. Immunol.*, 2000, 18:245-273.
Gallucci et al., "Natural adjuvants: Endogenous activators of dendritic cells," *Nature Medicine*, 1999, 5(11):1249-1255.
Gallucci and Matzinger, "Danger signals: SOS to the immune system," *Curr. Opin. Immunol.*, 2001, 13:114-119.
Granucci et al., "Transcriptional reprogramming of dendritic cells by differentiation stimuli," *Eur. J. Immunol.*, 2001, 31:2539-2546.
Gunzer et al., "Antigen Presentation in Extracellular Matrix: Interactions of T Cells with Dendritic Cells Are Dynamic, Short Lived, and Sequential," *Immunity*, 2000, 13:323-332.
Hogquist et al., "T Cell Receptor Antagonist Peptides Induced Positive Selection," *Cell*, 1994, 76:17-27.

(Continued)

*Primary Examiner*—Mary E. Mosher
(74) *Attorney, Agent, or Firm*—Fish & Richardson P.C., P.A.

(57) ABSTRACT

A molecule capable of potentiating immune responses is described, as well as methods for using the molecule to enhance immune responses and enhance dendritic cell function. Also described are compositions containing the molecule and methods for using the compositions to treat or immunize individuals.

21 Claims, 9 Drawing Sheets

OTHER PUBLICATIONS

Humphrey et al., "The origin of follicular dendritic cells in the mouse and the mechanism of trapping of immune complexes on them," *Eur. J. Immunol.*, 1984, 14:859-864.

Inaba et al., "High Levels of a Major Histocompatibility Complex II-Self Peptide Complex on Dendritic Cells from the T Cell Areas of Lymph Nodes," *J. Exp. Med.*, 1997, 186(5):665-672.

Ingulli et al., "In Vivo Detection of Dendritic Cell Antigen Presentation to CD4+ T Cells," *J. Exp. Med.*, 1997, 185(12):2133-2141.

Johnson et al., "Prevalent Class I-Restricted T-Cell Response to the Theiler's Virus Epitope $D^b$:$VP2_{121-130}$ in the Absence to Endogenous CD4 Help, Tumor Necrosis Factor Alpha, Gamma Interferon, Perforin, or Costimulation through CD28," *J. Virology*, 1999, 73(5):3702-3708.

Johnson et al., "Preservation of motor function by inhibition of CD8+ virus peptide-specific T cells in Theiler's virus infection," *FASEB J.*, 2001, 15:2760-2762.

Josien et al., "TRANCE, a Tumor Necrosis Factor Family Member, Enhances the Longevity and Adjuvant Properties of Dendritic Cells In Vivo," *J. Exp. Med.*, 2000, 191(3):495-501.

Kanto et al., "Ceramide Mediates Tumor-Induced Dendritic Cell Apoptosis," *J. Immunol.*, 2001, 167:3773-3784.

Koch et al., "Effective Enrichment of Murine Epidermal Langerhans Cells by a Modified (Mismatched) Panning Technique," *J. Invest. Dermatol.*, 1992, 99:803-807.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lang et al., "Isolation and Characterization of a Human Monoclonal Antibody That Recognizes Epitopes Shared by *Pseudomonas aeruginosa* Immunotype 1, 3, 4, and 6 Lipopolysaccharides," *Infection and Immunity*, 1989, 57(12):3851-3855.

Latchman et al., "PD-L2 is a second ligand for PD-1 and inhibits T cell activation," *Nature Immunol.*, 2001, 2(3):261-268.

Leenen et al., "Heterogeneity of Mouse Spleen Dendritic Cells: In Vivo Phagocytic Activity, Expression of Macrophage Markers, and Subpopulation Turnover," *J. Immunol.*, 1998, 160:2166-2173.

Lu et al., "Increased Apoptosis of Immunoreactive Host Cells and Augmented Donor Leukocyte Chimerism, Not Sustained Inhibition of B7 Molecule Expression are Associated with Prolonged Cardiac Allograft Survival in Mice Preconditioned with Immature Donor Dendritic Cells Plus Anti-CD40L mAb," *Transplantation*, 1999, 68(6):747-757.

Lutz et al., "An advanced culture method for generating large quantities of highly pure dendritic cells from mouse bone marrow," *J. Immunol. Meth.*, 1999, 223:77-92.

Maldonado-López et al., "CD8α and CD8α Subclasses of Dendritic Cells Direct the Development of Distinct T Helper Cells In Vivo," *J. Exp. Med.*, 1999, 189(3):587-592.

Maraskovsky et al., "Dramatic Increase in the Numbers of Functionally Mature Dendritic Cells in Flt3 Ligand-treated Mice: Multiple Dendritic Cell Subpopulations Identified," *J. Exp. Med.*, 1996, 184:1953-1962.

Matsue et al., "Dendritic Cells Undergo Rapid Apoptosis In Vitro During Antigen-Specific Interaction with CD4+ T Cells," *J. Immunol.*, 1999, 162:5287-5298.

Mayordomo et al., "Bone marrow-derived dendritic cells pulsed with synthetic tumour peptides elicit protective and therapeutic antitumour immunity," *Nature Medicine*, 1995, 1(12):1297-1302.

Miller et al., "Monoclonal Autoantibodies Promote Central Nervous System Repair in an Animal Model of Multiple Sclerosis," *J. Neurosci.*, 1994, 14(10):6230-6238.

Miller et al., "Multi-organ Reactivity of a Monoclonal Natural Autoantibody That Promotes Remyelination in a Mouse Model of Multiple Sclerosis," *J. Histochem. Cytochem.*, 1996, 44(9):1005-1011.

Mitsunaga et al., "Direct evidence that a human antibody derived from patient serum can promote myelin repair in a mouse model of chronic-progressive demyelinating disease," *FASEB J.*, 2002, 16(10):1325-1327.

Monks et al., "Three-dimensional segregation of supramolecular activation clusters in T cells," *Nature*, 1998, 395:82-86.

Murphy et al., "Induction by Antigen of Intrathymic Apoptosis of CD4+ CD8+ $TCR^{lo}$ Thymocytes in Vivo," *Science*, 1990, 250:1720-1722.

Nociari et al. "A novel one-step, highly sensitive fluorometric assay to evaluate cell-mediated cytotoxicity," *J. Immunol. Meth.*, 1998, 213:157-167.

Nonacs et al., "Mechanisms of Mouse Spleen Dendritic Cell Function in the Generation of Influenza-specific, Cytolytic T Lymphocytes," *J. Exp. Med.*, 1992, 176:519-529.

Pease et al., "Spontaneous H-2 mutants provide evidence that a copy mechanism analogous to gene conversion generates polymorphism in the major histocompatibility complex," *Proc. Natl. Acad. Sci. USA*, 1983, 80:242-246.

Plotnicky-Gilquin, "Differential Effects of Parainfluenza Virus Type 3 on Human Monocytes and Dendritic Cells," *Virology*, 2001, 285:82-90.

Poltorak et al., "Defective LPS Signaling in C3H/HeJ and C57BL/10ScCr Mice: Mutations in Tlr4 Gene," *Science*, 1998, 282:2085-2088.

Pulendran et al., "Developmental Pathways of Dendritic Cells in Vivo," *J. Immunol.*, 1997, 159:2222-2231.

Pulendran et al., "Sensing Pathogens and Tuning Immune Responses," *Science*, 2001, 293:253-256.

Rötzschke et al., "Exact prediction of a natural T cell epitope," *Eur. J. Immunol.*, 1991, 21:2891-2894.

Steinman and Witmer, "Lymphoid dendritic cells are potent stimulators of the primary mixed leukocyte reaction in mice," *Proc. Natl. Acad. Sci. USA*, 1978, 75(10):5132-5136.

Strunk et al., "A Skin Homing Molecule Defines the Langerhans Cell Progenitor in Human Peripheral Blood," *J. Exp. Med.*, 1997, 185(6):1131-1136.

Tallquist et a., "A Single T Cell Receptor Recognizes Structurally Distinct MHC/Peptide Complexes with High Specificity," *J. Exp. Med.*, 1996, 184:1017-1026.

Tseng et al., "B7-DC, a New Dendritic Cell Molecule with Potent Costimulatory Properties for T Cells," *J. Exp. Med.*, 2001, 193(7):839-845.

Vremec et al., "The Surface Phenotype of Dendritic Cells Purified from Mouse Thymus and Spleen: Investigation of the CD8 Expression by a Subpopulation of Dendritic Cells," *J. Exp. Med.*, 1992, 176:47-58.

Vremec and Shortman, "Dendritic Cell Subtypes in Mouse Lymphoid Organs," *J. Immunol.*, 1997, 159:565-573.

Vremec et al., "CD4 and CD8 Expression by Dendritic Cell Subtypes in Mouse Thymus and Spleen," *J. Immunol.*, 2000, 164:2978-2986.

Warrington et al., "Human monoclonal antibodies reactive to oligodendrocytes promote remyelination in a model of multiple sclerosis," *Proc. Natl. Acad. Sci. USA*, 2000, 97(12):6820-6825.

Warrington et al., "Immunoglobulin-mediated CNS repair," *J. Allergy Clin. Immunol.*, 2001, 108:S121-S125.

Winzler et al., "Maturation Stages of Mouse Dendritic Cells in Growth Factor-dependent Long-Term Cultures," *J. Exp. Med.*, 1997, 185(2):317-328.

Woodhead et al., "Novel molecular mechanisms of dendritic cell-induced T cell activation," *Int. Immunol.*, 2000, 12(7):1051-1061.

Wu et al., "Thymic Dendritic Cell Precursors: Relationship to the T Lymphocyte Lineage and Phenotype of the Dendritic Cell Progeny," *J. Exp. Med.*, 1996, 184:903-911.

Wu et al. "Derivation of Dendritic Cells from Myeloid and Lymphoid Precursors," *Intern. Rev. Immunol.*, 2001, 20:117-135.

Wülfing and Davis, "A Receptor/Cytoskeletal Movement Triggered by Costimulation During T Cell Activation," *Science*, 1998, 282:2266-2269.

Yoshida et al., "Host origin of follicular dendritic cells induced in the spleen of SCID mice after transfer of allogeneic lymphocytes," *Immunology*, 1995, 84:117-126.

Young and Steinman, "Dendritic Cells Stimulate Primary Human Cytolytic Lymphocyte Responses in the Absence of CD4+ Helper T Cells," *J. Exp. Med.*, 1990, 171:1315-1332.

Greenwald et al., "Negative co-receptors in lymphocytes," *Current Opinion in Immunology*, 2002, 14:391-396.

Liang and Sha, "The right place at the right time: novel B7 family members regulate effector T cell responses," *Current Opinion in Immunology*, 2002, 14:384-390.

Nguyen et al., "Cross-linking the B7 Family Molecule B7-DC Directly Activates Immune Functions of Dendritic Cells," *J. Exp. Med.*, 2002, 196:1393-1398.

* cited by examiner

PD-1 sHIgM12

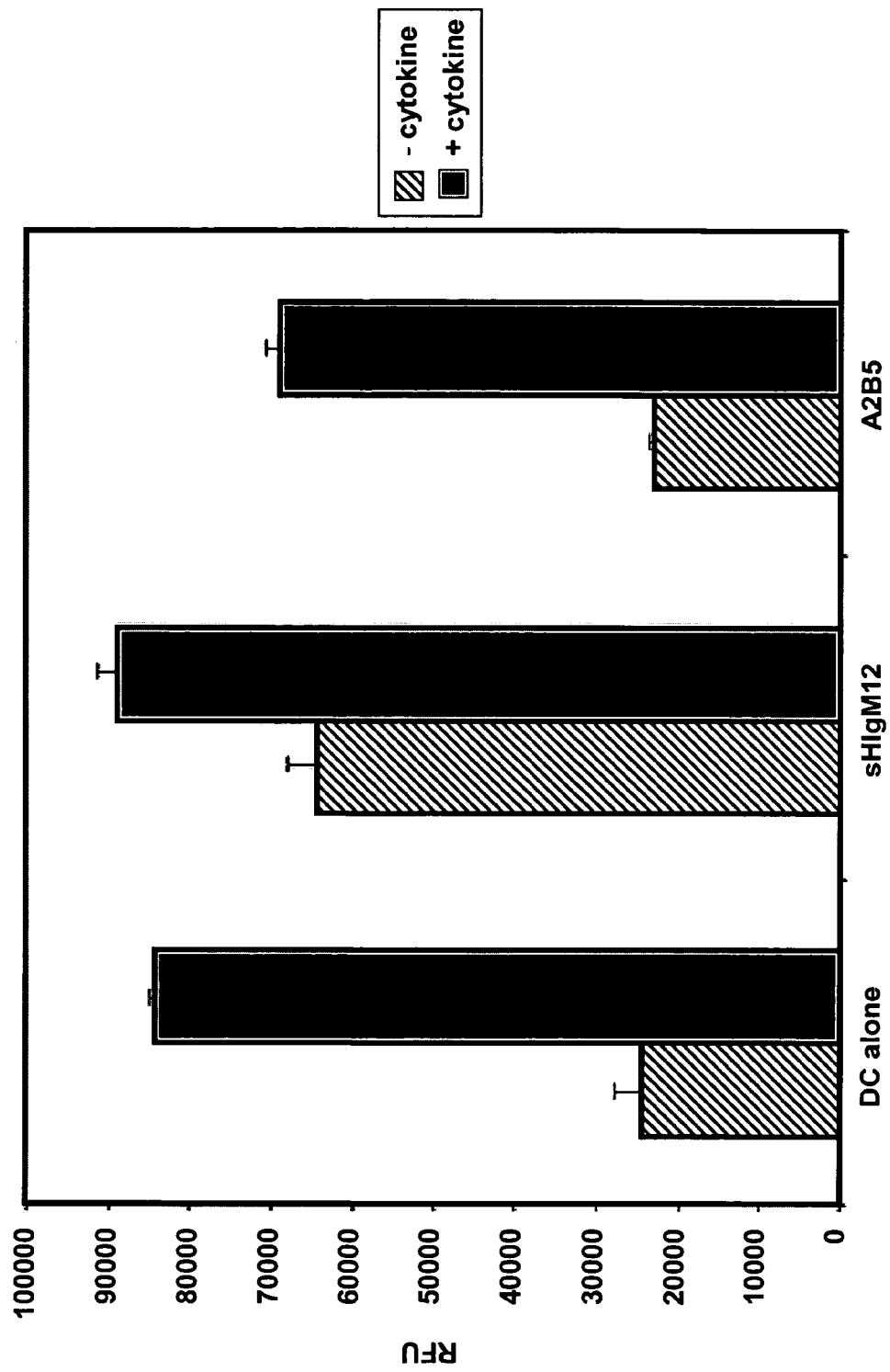

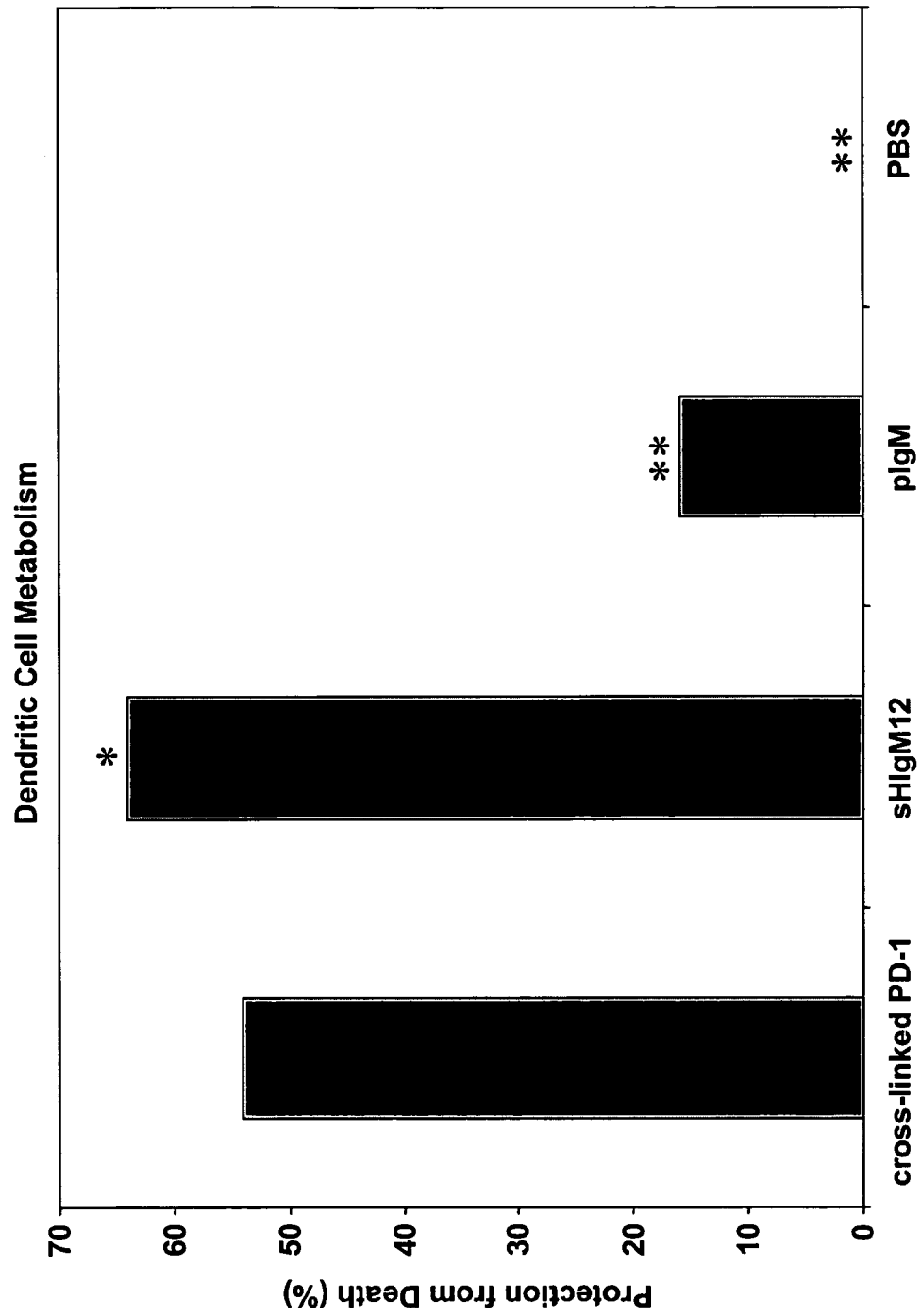

DENDRITIC CELL POTENTIATION

TECHNICAL FIELD

This invention relates to methods for enhancing immune responses, and more particularly to enhancing immune responses by prolonging dendritic cell longevity.

BACKGROUND

Decavalent IgM antibodies display measurable binding avidity to antigens, even though binding affinity may be low. The multivalent structure of pentameric IgM provides the potential for cross-linking cell surface targets, endowing the soluble antibodies with biological potential not normally associated with immune function.

Dendritic cells are efficient antigen-presenting cells (APC). These cells express class I and class II major histocompatibility complex (MHC) peptide-presenting molecules on their cell surfaces, along with a series of costimulatory molecules (Banchereau and Steinman (1998) *Nature* 392:245–252). Naïve T cells express receptors for these dendritic cell ligands. Following recognition of peptide-antigen presented in the context of class I or class II molecules, the structure of the T cell membrane is reorganized, bringing together the elements of the T cell receptor with other cell-surface molecules, including the co-receptors CD4 or CD8 and the costimulatory receptors CD28 and CTLA-4 (Monks et al. (1998) *Nature* 395:82–86; and Wulfing and Davis (1998) *Science* 282:2266–2269). Interactions within the newly formed macromolecular complexes determine the outcome of inductive events transduced into T cells by dendritic cells.

Dendritic cells reside in a variety of tissues and display distinct tissue-associated phenotypes (Strunk et al. (1997) *J. Exp. Med.* 185:1131–1136; Caux et al. (1996) *J. Exp. Med.* 184:695–706; Wu et al. (1996) *J. Exp. Med.* 184:903–911; and Vremec et al. (1992) *J. Exp. Med.* 176:47–58). The relationships among the cell lineages of these different subsets of cells are not firmly established. A large body of work has emerged focusing on dendritic cells generated in vitro from bone marrow or blood precursors (Mayordomo et al. (1995) *Nat. Med.* 1:1297–1302; Nonacs et al. (1992) *J. Exp. Med.* 176:519–529; Steinman and Witmer (1978) *Proc. Natl. Acad. Sci. USA* 75:5132–5136; and Young and Steinman (1990) *J. Exp. Med.* 171:1315–1332). The cells generated in vitro express high levels of class I antigens and the series of costimulatory ligands associated with endogenous dendritic cells (Fagnoni et al. (1995) *Immunology* 85:467–474; and Bancereau et al. (2000) *Annu. Rev. Immunol.* 18:767-811). Importantly, they are able to efficiently activate naïve T cells, a function that is the signature of the dendritic cell. A method for clinically promoting dendritic cells to stimulate T cell activation would be useful to treat immunocompromised patients.

SUMMARY

A challenge in harnessing the immune response is to direct immunity against specific antigens associated with tumors or known pathogens. Often, however, these antigens are weak and do not result in a strong immune response. The invention described herein provides a direct way to use purified or recombinant proteins to induce potent immune responses. The procedure can be used to generate vaccines to a variety of pathogens, and to bolster immunotherapy protocols for the treatment of existing diseases where the objective is to increase immune responsiveness.

This invention is based on the identification of a human IgM antibody (sHIgM12) that binds mouse dendritic cells and can induce dramatic immunopotentiation. This antibody has the ability to potentiate immune responses against protein or tumor antigens when administered without other adjuvants. The antibody induces intracellular signaling changes in dendritic cells grown and differentiated in vitro, and protects dendritic cells from death caused by deprivation of growth and survival factors. Antibodies such as sHIgM12 and other molecules having similar functions therefore may have substantial therapeutic value, and in particular can be used to enhance immune responses against pathogens and cancers. These molecules also are useful in vaccination of humans and other mammals against tumors and pathogens by potentiating the immunity of individuals to purified proteins.

The invention also is based on the discovery that the programmed death-1 (PD-1) polypeptide also can enhance the function of dendritic cells. Dendritic cells incubated with immobilized PD-1, for example, can be administered to a subject in order to potentiate an immune response. Polypeptides such as immobilized PD-1 therefore also may have substantial therapeutic value.

The invention features a purified molecule that binds specifically to B7-DC polypeptides on a cell. The binding can result in cross-linking of a plurality of B7-DC polypeptides, and the molecule can potentiate an immune response upon administration to a mammal. The purified molecule can be a polypeptide such as an antibody. The antibody can be an IgM antibody. The IgM antibody can have the epitope specificity of sHIgM12, or can be sHIgM12. The antibody can be a cross-linked, multivalent IgG, IgA, IgD, or IgE complex. The purified molecule can be a polypeptide (e.g., PD-1) immobilized on a solid substrate. The cell can be a dendritic cell or a tumor cell (e.g., a glioma tumor cell). The administration can be by injection. The mammal can be a human.

In another aspect, the invention features a purified molecule that binds specifically to B7-DC polypeptides on a cell, wherein such binding can result in cross-linking of a plurality of said B7-DC polypeptides, and wherein dendritic cells contacted with the molecule exhibit at least one characteristic selected from the group consisting of prolonged longevity, increased NF-κB expression, increased NF-κB translocation to the nucleus, increased ability to activate naïve T cells, increased phosphorylation of Akt, increased localization to lymph nodes upon administration to a mammal, maintenance of metabolic rate in culture after cytokine withdrawal, and increased IL-12 secretion. The activation of naïve T cells can be measured by detection of one or both of CD44 and CD69 on the T cells, or by incorporation of $^3$H-thymidine into the T cells.

In another aspect, the invention features a composition containing the purified molecule. The composition can further contain an antigen, wherein the antigen is capable of eliciting an immune response when the composition is administered to a mammal. The antigen can be a tumor antigen or an antigen from a pathogen. The antigen can be a component of a killed virus or a component of a killed bacterium. The antigen can be a killed virus or a killed bacterium. The mammal can be a human. The composition can further contain dendritic cells.

In yet another aspect, the invention features a composition containing a polypeptide immobilized on a solid substrate. The immobilized polypeptide can bind specifically to and cross-link a plurality of B7-DC polypeptides on a cell. Dendritic cells contacted with the immobilized polypeptide can exhibit at least one characteristic selected from the group consisting of prolonged longevity, increased NF-κB expression, increased NF-κB translocation to the nucleus, increased ability to activate naïve T cells, increased phosphorylation of Akt, increased localization to lymph nodes upon administration to a mammal, maintenance of metabolic rate in culture after cytokine withdrawal, and increased IL-12 secretion. The immobilized polypeptide can be PD-1. The composition can further contain dendritic cells.

The invention also features a method of enhancing dendritic cell function in a mammal. The method can include administering to the mammal a composition of the invention. The enhancing of dendritic cell function can involve prolonging the longevity of the dendritic cells.

In another aspect, the invention features a method of potentiating an immune response in a mammal. The method can include administering to the mammal a composition of the invention.

The invention also features a method of treating a tumor in a mammal. The method can involve administering to the mammal a composition of the invention.

In yet another aspect, the invention features a method of inducing immunity to a pathogen in a mammal. The method can include administering a composition of the invention to the mammal.

In another aspect, the invention features a method of potentiating an immune response in a mammal. The method can include contacting dendritic cells of mammal in vitro with a composition of the invention, and transferring the contacted dendritic cells into the mammal.

The invention also features an isolated nucleic acid encoding the molecule of the invention, a vector containing the nucleic acid of the invention, and a host cell containing the vector of the invention.

In yet another aspect, the invention features articles of manufacture containing the molecules and compositions of the invention. The articles of manufacture can further contain an antigen. The antigen can be capable of eliciting an immune response.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7A is a column graph showing levels of dendritic cell metabolism before and after cytokine withdrawal from untreated cells and cells treated with either sHIgM12 or a control antibody as indicated. FIG. 7B is a column graph showing levels of dendritic cell metabolism before and after cytokine withdrawal from untreated cells and cells treated with either immobilized PD-1.Ig, sHIgM12, or a control antibody as indicated.

DETAILED DESCRIPTION

1. Molecules

Figure 1:
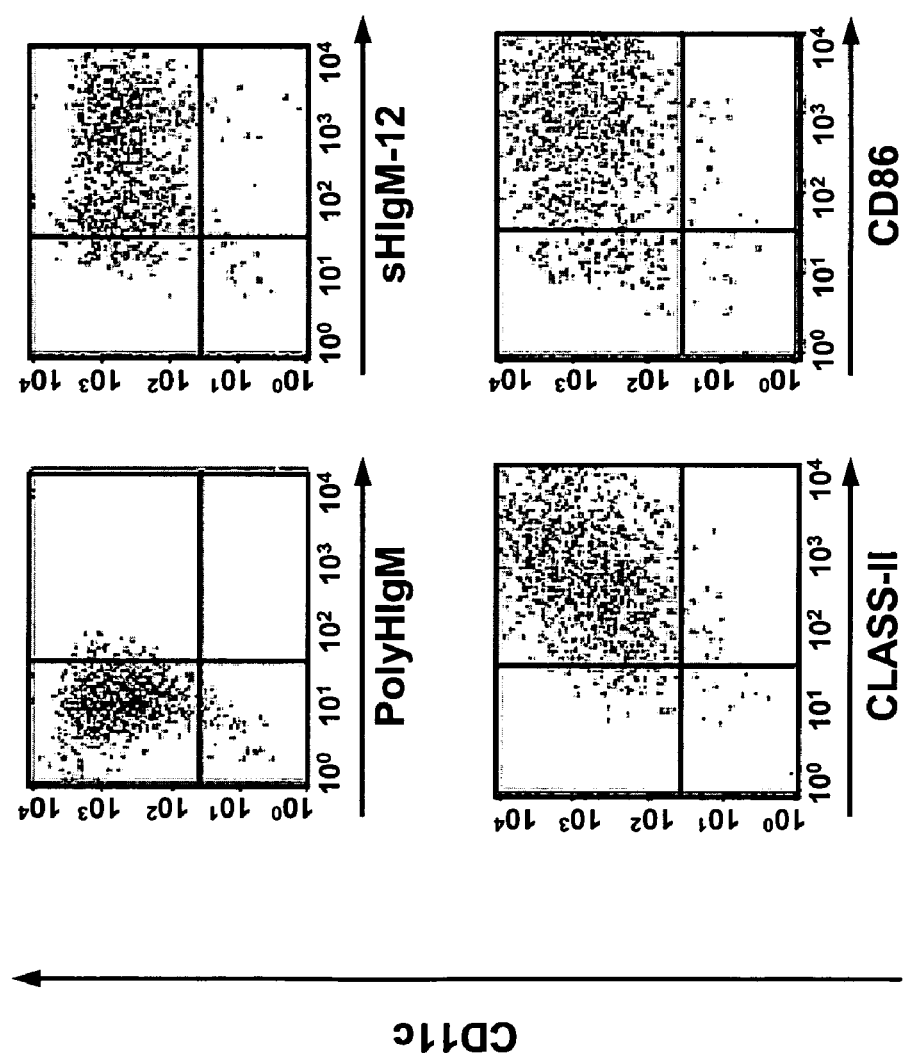
FIG. 1 is a series of fluorescence-activated cell sorting (FACS) plots showing the staining of bone marrow-derived murine dendritic cells with sHIgM12 or polyclonal human IgM as indicated (upper panels), followed by fluorescein isothiocyanate- (FITC-) conjugated α-human IgM. Cells also were costained with phycoerythrin- (PE-) conjugated α-CD11c. The lower panels show staining with antibodies against typical dendritic cell surface markers, including MHC class II and CD86.

The invention provides molecules that bind specifically to B7-DC polypeptides. Such molecules can bind simultaneously to a plurality of B7-DC polypeptides (i.e., one such molecule can bind to more than one B7-DC polypeptide at the same time). Molecules provided herein thus can effectively cross-link a plurality of B7-DC polypeptides. Molecules of the invention typically are polypeptides, and antibodies can be particularly useful (see below).

Molecules of the invention can bind specifically to cells through B7-DC polypeptides that are present on the cell surface. As used herein, "binds specifically to B7-DC" means that a molecule binds preferentially to B7-DC and does not display significant binding to other cell surface polypeptides (e.g., substantially less, or no, detectable binding to other cell surface polypeptides). Molecules (e.g., antibodies or polypeptides) can be tested for recognition of B7-DC by standard immunoassay methods, including FACS, enzyme-linked immunosorbent assay (ELISA), and radioimmuno assay (RIA). See, e.g., *Short Protocols in Molecular Biology*, eds. Ausubel et al., Green Publishing Associates and John Wiley & Sons (1992).

B7-DC is a cell surface polypeptide that can be found on, for example, dendritic cells and some tumor cells (e.g., glioma tumor cells). Molecules of the invention can bind to B7-DC on the surface of dendritic cells in a mammal (e.g., a human) and potentiate an immune response. As used herein, the term "potentiate an immune response" encompasses enhancement of dendritic cell function and increased activation of naïve T cells. Enhanced dendritic cell function includes components such as prolonged longevity of dendritic cells, which can be detected based on increased expression of NF-κB and increased translocation of NF-κB to the nucleus. Other components of enhanced dendritic cell function include an increased ability of dendritic cells to activate naïve T cells, increased localization of dendritic cells to the lymph nodes, increased phosphorylation of Akt (also known as protein kinase B) within dendritic cells, and increased secretion of interleukin-12 (IL-12) by dendritic cells. Molecules provided by the invention also can enhance the metabolism of dendritic cells upon the withdrawal of cytokines from dendritic cells in culture. The molecules described herein can be administered to a mammal (e.g., a human) in order to enhance dendritic cell function and potentiate an immune response that can include any or all of the above-listed components. Molecules of the invention also can be used to contact and activate dendritic cells in vitro.

Potentiation of an immune response by molecules of the invention can be measured by assessing any of the components listed above. Secretion of IL-12 can be measured, for example, by an enzyme linked immunosorbent (ELISA) assay as described in the Examples (below). Activation of naïve T cells can be assayed by, for example, measuring the incorporation of $^3$H-thymidine into newly synthesized DNA in proliferating cells, or by detecting T cell activation markers such as CD44 and/or CD69. Expression or translocation of NF-κB can be measured by, for example, cell staining with an antibody against NF-κB. Increased phosphorylation of Akt can be assessed by, for example, western blotting with an antibody against phosphorylated Akt. Antibodies against NF-κB and phosphorylated Akt are available from, for example, Cell Signaling Technologies, Inc. (Beverly, Mass.). Methods for measuring the other components encompassed by enhanced dendritic cell function and immunopotentiation also are described herein.

The molecules provided by the invention typically are purified. The term "purified" as used herein refers to a molecule that has been separated or isolated from other cellular components by which it is naturally accompanied (e.g., other cellular proteins, polynucleotides, or cellular components), or separated from other components present in a reaction mixture when the molecule is synthesized in vitro. "Purified" as used herein also encompasses molecules that are partially purified, so that at least some of the components by which the molecule is accompanied are removed. Typically, a molecule is considered "purified" when it is at least 50% (e.g., 55%, 60%, 70%, 80%, 90%, 95%, or 99%), by dry weight, free from the proteins and other organic molecules or components with which it naturally associates or with which it is accompanied in a synthesis reaction.

2. Polypeptides and Antibodies

Molecules of the invention can be polypeptides. As used herein, a polypeptide is an amino acid chain, regardless of length or post-translational modification (e.g., phosphorylation or glycosylation). The polypeptides provided herein can bind specifically to B7-DC, and upon administration to a mammal (e.g., a human), can enhance dendritic cell function and potentiate an immune response. Polypeptides of the invention also can enhance dendritic cell function when incubated in vitro with dendritic cells.

PD-1 is a polypeptide that is a natural receptor for B7-DC. PD-1 can be immobilized on a solid substrate (e.g., a plastic dish or a glass microscope slide). Upon incubation with dendritic cells, immobilized PD-1 can cross-link a plurality of B7-DC polypeptides on the cell surface and enhance the function of the dendritic cells. Incubation of cultured dendritic cells with immobilized PD-1 can, for example, maintain the metabolic rate of the cells upon removal of cytokines from the culture medium, as compared to the metabolic rate of dendritic cells that are not incubated with PD-1 (see Example 7).

Molecules of the invention can be antibodies that have specific binding activity for B7-DC. The terms "antibody" and "antibodies" encompass intact molecules as well as fragments thereof that are capable of binding to B7-DC. An antibody can be of any immunoglobulin (Ig) class, including IgM, IgA, IgD, IgE, and IgG, and any subclass thereof. Antibodies of the IgM class (e.g., sHIgM12) typically are pentavalent and are particularly useful because one antibody molecule can cross-link a plurality of B7-DC polypeptides. Immune complexes containing Ig molecules that are cross-linked (e.g., cross-linked IgG) and are thus multivalent also are capable of cross-linking a plurality of B7-DC molecules, and can be particularly useful.

As used herein, an "epitope" is a portion of an antigenic molecule to which an antibody binds. Antigens can present more than one epitope at the same time. For polypeptide antigens, an epitope typically is about four to six amino acids in length. Two different immunoglobulins can have the same epitope specificity if they bind to the same epitope or set of epitopes.

The terms "antibody" and "antibodies" include polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen.

Polyclonal antibodies are contained in the sera of immunized animals. Monoclonal antibodies can be prepared using, for example, standard hybridoma technology. In particular, monoclonal antibodies can be obtained by any technique that provides for the production of antibody molecules by continuous cell lines in culture as described, for example, by Kohler et al. (1975) *Nature* 256:495–497, the human B-cell hybridoma technique of Kosbor et al. (1983) *Immunology Today* 4:72, and Cote et al. (1983) *Proc. Natl. Acad. Sci. USA* 80:2026–2030, and the EBV-hybridoma technique of Cole et al., *Monoclonal Antibodies and Cancer Therapy*, Alan R. Liss, Inc. pp. 77–96 (1983). A hybridoma producing monoclonal antibodies of the invention can be cultivated in vitro or in vivo.

Antibodies of the invention also can be isolated from, for example, the serum of an individual. The sHIgM12 antibody, for example, was isolated from human serum as described in Example 1 herein. Suitable methods for isolation include purification from mammalian serum using techniques that include, for example, chromatography.

Antibodies that bind to B7-DC also can be produced by, for example, immunizing host animals (e.g., rabbits, chickens, mice, guinea pigs, or rats) with B7-DC. A B7-DC polypeptide or a portion of a B7-DC polypeptide can be produced recombinantly, by chemical synthesis, or by purification of the native protein, and then used to immunize animals by injection of the polypeptide. Adjuvants can be used to increase the immunological response, depending on the host species. Suitable adjuvants include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Standard techniques can be used to isolate antibodies generated in response to the B7-DC immunogen from the sera of the host animals. Such techniques are useful for generating antibodies that have similar characteristics to sHIgM12 (e.g., similar epitope specificity and other functional similarities).

Antibodies such as sHIgM12 also can be produced recombinantly. The amino acid sequence (e.g., the partial amino acid sequence) of an antibody provided herein can be determined by standard techniques, and a cDNA encoding the antibody or a portion of the antibody can be isolated from the serum of the subject (e.g., the human patient or the immunized host animal) from which the antibody was originally isolated. The CDNA can be cloned into an expression vector using standard techniques. The expression vector then can be transfected into an appropriate host cell (e.g., a Chinese hamster ovary cell, a COS cell, or a hybridoma cell), and the antibody can be expressed and purified. See, for example, Example 9 herein.

Antibody fragments that have specific binding affinity for B7-DC and retain cross-linking function also can be generated by techniques such as those disclosed above. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989) *Science* 246:1275–1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778. Such fragments can be rendered multivalent by, for example, biotinylation and cross-linking, thus generating antibody fragments that can cross-link a plurality of B7-DC polypeptides.

3. Nucleic Acids, Vectors, and Host Cells

The invention provides nucleic acids encoding molecules (e.g., polypeptides and antibodies) that bind specifically to B7-DC. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids of the invention include, for example, cDNAs encoding the light and heavy chains of the sHIgM12 antibody.

An "isolated nucleic acid" refers to a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The isolated nucleic acid molecules provided herein can be produced by standard techniques, including, without limitation, common molecular cloning and chemical nucleic acid synthesis techniques. For example, polymerase chain reaction (PCR) techniques can be used to obtain an isolated nucleic acid molecule encoding sHIgM12. Isolated nucleic acids of the invention also can be chemically synthesized, either as a single nucleic acid molecule (e.g., using automated DNA synthesis in the 3' to 5' direction using phosphoramidite technology) or as a series of polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded nucleic acid molecule per polynucleotide pair.

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, a nucleic acid (e.g., a nucleic acid encoding the light and/or heavy chains of sHIgM12) is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors provided herein thus are useful to produce sHIgM12, as well as other molecules of the invention.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available (e.g., Lipofectin® (Invitrogen/Life Technologies); Fugene (Roche, Indianapolis, Ind.); and SuperFect (Qiagen, Valencia, Calif.)).

4. Compositions

The invention provides compositions containing the molecules described herein (e.g., antibodies such as sHIgM12 and polypeptides such as PD-1). Such compositions are suitable for administration to a subject to enhance dendritic cell function and potentiate an immune response. As described above, enhanced dendritic cell function includes such components as prolonged longevity, increased ability to activate naïve T cells, increased localization to the lymph nodes, increased phosphorylation of Akt, and increased secretion of interleukin-12 (IL-12).

Compositions provided herein also can contain a molecule (e.g., PD-1) that is immobilized on a solid substrate. Such compositions can be used to contact dendritic cells and enhance their function as described above.

Methods for formulating and subsequently administering therapeutic compositions are well known to those skilled in the art. Dosages typically are dependent on the responsiveness of the subject to the molecule, with the course of treatment lasting from several days to several months, or until a suitable immune response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Dosage typically is from 0.01 μg to 100 g per kg of body weight (e.g., from 1 μg to 100 mg, from 10 μg to 10 mg, or from 50 μg to 500 μg per kg of body weight). Compositions containing the molecules provided herein may be given once or more daily, weekly, monthly, or even less often.

In addition to the molecules provided herein, compositions of the invention further can contain antigens that will elicit a specific immune response. Suitable antigens include, for example, polypeptides or fragments of polypeptides expressed by tumors and pathogenic organisms. Killed viruses and bacteria, in addition to components of killed viruses and bacteria, also are useful antigens. Such antigens can stimulate immune responses against tumors or pathogens.

Compositions provided herein also can include dendritic cells that have been isolated from, for example, bone marrow, spleen, or thymus tissue. Dendritic cell lines also can be useful in compositions of the invention.

Molecules of the invention can be admixed, encapsulated, conjugated or otherwise associated with other molecules, molecular structures, or mixtures of compounds such as, for example, liposomes, receptor targeted molecules, or oral, topical or other formulations for assisting in uptake, distribution and/or absorption.

Pharmaceutically acceptable carriers are pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules provided herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous drip); oral; topical (e.g., transdermal, sublingual, ophthalmic, or intranasal); or pulmonary (e.g., by inhalation or insufflation of powders or aerosols). Administration can be rapid (e.g., by injection) or can occur over a period of time (e.g., by slow infusion or administration of slow release formulations). For administration to the central nervous system, antibodies can be injected or infused into the cerebrospinal fluid, typically with one or more agents capable of promoting penetration across the blood-brain barrier.

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Molecules of the invention can encompass any pharmaceutically acceptable salts, esters, or salts of such esters, or any other compound which, upon administration to a subject, is capable of providing (directly or indirectly) the biologically active metabolite or residue thereof. Accordingly, for example, the invention provides pharmaceutically acceptable salts of molecules such as antibodies (e.g., sHIgM12), prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the antibodies useful in methods of the invention (i.e., salts that retain the desired biological activity of the parent antibodies without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the PNA components within the compositions of the present invention.

Pharmaceutical formulations of the present invention, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the antibody(s) contained in the formulation.

Compositions of the present invention can be formulated into any of many possible dosage forms such as, without limitation, tablets, capsules, liquid syrups, soft gels, suppositories, and enemas. Compositions also can be formulated as suspensions in aqueous, non-aqueous or mixed media. Aqueous suspensions further can contain substances that increase the viscosity of the suspension including, for example, sodium carboxymethyl-cellulose, sorbitol, and/or dextran. Suspensions also can contain stabilizers.

5. Methods of Using the Molecules Provided Herein to Potentiate an Immune Response The invention provides methods for using molecules described herein to enhance dendritic cell function and potentiate an immune response. Molecules of the invention can interact specifically with B7-DC and, as described herein, can enhance the function of dendritic cells and potentiate an immune response. Methods of the invention are particularly useful for treating tumors and inducing immunity to a specific antigen.

The methods provided herein typically involve administering to a mammal (e.g., a human) a molecule of the invention (e.g., an antibody such as sHIgM12) or a composition of the invention (e.g., a composition containing sHIgM12). Methods of the invention also involve administration of dendritic cells that have been contacted with a molecule or a composition provided herein (e.g., a composition containing sHIgM12 and an antigen). Such dendritic cells are useful to potentiate an immune response in the mammal to which they are administered.

As described above, the molecule, composition, or activated dendritic cells can be administered by any suitable systemic or local method. Systemic methods of administration include, without limitation, oral, topical, or parenteral administration, as well as administration by injection. Local methods of administration include, for example, direct injection into a tumor.

Methods of the invention can be used to enhance dendritic cell function. The enhancement of dendritic cell function includes, for example, prolonging the longevity of dendritic cells, increasing the ability of dendritic cells to activate naïve T cells, and increasing the localization of dendritic cells to lymph nodes in a mammal. The longevity of dendritic cells can be assessed by, for example, measuring the expression of NF-κB or the translocation of NF-κB to the nucleus. Since NF-κB is an intracellular signal involved in the inhibition of programmed cell death, increased expression or translocation of NF-κB indicates inhibition of apoptosis and prolonged dendritic cell longevity. T cell activation can be measured by, for example, assessing the incorporation of radiolabeled (e.g., tritiated) thymidine into newly synthesized DNA in proliferating T cells. Activation of naïve T cells also can be measured by detecting (e.g., by flow cytometry) CD44 and/or CD69 activation markers on the T cell surface.

Methods for potentiating an immune response (i.e., inducing immunity to a particular antigen) can involve administering to a mammal (e.g., a human) a composition that contains (1) a purified molecule (e.g., a polypeptide or an antibody, particularly sHIgM12) capable of binding specifically to B7-DC polypeptides, and (2) an antigen (e.g., an antigen from a tumor cell or from a pathogen). Such methods also can involve administering dendritic cells that have been activated in vitro by contacting the cells with (1) a purified molecule (e.g., a polypeptide or an antibody such as sHIgM12) capable of binding specifically to B7-DC polypeptides, and (2) an antigen (e.g., an antigen from a tumor cell or from a pathogen). These methods are useful to, for example, treat tumors and/or induce immunity to pathogens.

Methods of the invention can be useful for treating solid tumors including, without limitation, breast cancer, lung cancer, pancreatic cancer, brain cancer, prostate cancer, ovarian cancer, uterine cancer, renal cancer, melanoma, and other solid tumors. Such methods are particularly useful for treating melanoma and renal carcinoma tumors. A solid tumor can be, for example, an early-stage solid tumor. As used herein, the term "treating a tumor" encompasses reducing the size of a tumor, reducing the number of viable cells in a tumor, and/or slowing or stopping the growth of a tumor. Methods for assessing such outcomes are known in the art. Methods for treating tumors can involve administration of a molecule or composition of the invention (e.g., a composition containing sHIgM12 and a tumor antigen) either systemically (e.g., intravenously or subcutaneously) or directly to a tumor (e.g., by injection).

7. Articles of Manufacture

The invention provides articles of manufacture that can include the molecules and/or compositions provided herein. The molecules and/or compositions can be combined with packaging material and sold as kits for potentiating an immune response in an individual. Components and methods for producing articles of manufacture are well known. Articles of manufacture may combine one or more of the molecules set out in the above sections. An article of manufacture can contain a composition that includes a molecule provided herein (e.g., an antibody such as sHIgM12 or a polypeptide such as immobilized PD-1). An article of manufacture also can include one or more antigens (e.g., a tumor antigen or an antigen from a pathogen) that can stimulate a specific immune response. Furthermore, an article of manufacture can contain dendritic cells. An article of manufacture also may include, for example, buffers or other control reagents for potentiating an immune response. Instructions describing how the molecules, antigens, dendritic cells, and compositions are effective for potentiating an immune response can be included in such kits.

The invention will be further described in the following examples, which do not limit the scope of the invention described in the claims.

EXAMPLES

Example 1

Materials and Methods

Isolation of human antibodies—Human serum samples were obtained from the dysproteinemia clinic, and those exhibiting an Ig clonal peak of greater than 20 mg/ml were chosen for further evaluation. The selected samples were from 50 patients with a wide variety of conditions characterized by a monoclonal IgM spike, including Waldenstrom's macroglobulinemia, lymphoma, and monoclonal gammopathy of undetermined significance. Sera were dialyzed against water, and precipitates were collected by centrifugation at 14,000 rpm for 30 minutes and dissolved in phosphate buffered saline (PBS). The samples were centrifuged and chromatographed on a Superose-6 column (Amersham Pharmacia, Piscataway, N.J.). IgM fractions were pooled and analyzed by SDS-PAGE, and protein concentrations were determined by reading absorbance at 280 nm. IgM solutions were sterile filtered and cryopreserved. The antibody sHIgM12 was identified based on its ability to bind dendritic cells as determined by FACS analysis (see Example 2). The polyclonal human IgM antibody control was described previously (Miller et al. (11994) *J. Neurosci.* 14:6230–6238).

Monomeric sHIgM12 was obtained from the pentameric form by reduction with 5 mM dithiothreitol (Sigma-Aldrich, St. Louis, Mo.) in 200 mM Tris, 150 mM NaCl, 1 mM EDTA pH 8.0 for 2 hours at room temperature. Subsequent alkylation was performed with 12 mM iodacetamide for 1 hour on ice. IgM monomers were isolated by chromatography on a Superdex-200 column (Amersham Pharmacia) equilibrated with PBS, and characterized by reducing and non-reducing SDS-PAGE.

Mice and reagents–C57BL6/J, C3H/HeJ, and BALB/C mouse strains were obtained from The Jackson Laboratory (Bar Harbor, Me.). OT-1 and D0-11 transgenic mouse strains (Hogquist et al. (1994) *Cell* 76:17–27; and Murphy et al. (1990) *Science* 250:1720–1723) were bred and maintained at the Mayo Clinic animal facility according to the protocol approved by the Institutional Review Board for Animal Rights, Mayo Clinic. C57BL/6-RAG$^{-/-}$ mice, CD4$^{-/-}$ mice, and GFP transgenic mice were purchased from The Jackson Laboratory (Bar Harbor, Me.). K$^-$D$^-$ mice were obtained from Francois Lemmonier, Pasteur Institute, Paris. Chicken ovalbumin was obtained from Sigma-Aldrich. Peptides were synthesized at the Mayo Protein Core Facility. Fluorophore-coupled anti-CD11c(HL-3), anti-B220(RA3-6B2), anti-CD80(16-10A1), anti-CD86(GL-1), anti-CD44(IM7), anti-CD 69(H1.2F3), anti-CD3e(145-2C11), anti-Mac1(M1/70), Pan-NK antibody(DX-5), anti-K$^b$(AF6-88.5), and anti-I-A$^b$ (KH74) were obtained from BD PharMingen (San Diego, Calif.). FITC-coupled goat anti-human IgM was obtained from Jackson ImmunoResearch Laboratories, Inc. (West Grove, Pa.). The $K^b$-Ser-Ile-Ile-Asn-Phe-Glu-Lys-Leu (SEQ ID NO:1) tetramer coupled to APC was prepared as previously described (Block et al. (2001) *J. Immunol.* 167: 821–826). RPMI-1640 medium was purchased from Gibco/Invitrogen (Carlsbad, Calif.).

Generation of immature and mature dendritic cells in vivo—Dendritic cells from bone marrow were isolated using an established protocol. Briefly, bone marrow was isolated from mouse hind leg long bones. Erythrocytes were lysed by treatment with ammonium chloride-potassium chloride (ACK; 0.1 M $NH_4Ac$, 0.01 M $KHCO_3$, 60 μM EDTA) at 37° C. The remaining cells were plated at a density of $1 \times 10^6$ cells per ml in 6 well plates (Becton Dickinson, Franklin Lakes, N.J.) in RPMI-10 containing 10 μg/ml murine granulocyte macrophage-colony stimulating factor (GM-CSF; PeproTech, Inc., Rocky Hill, N.J.) and 1 ng/ml murine interleukin-4 (IL-4; PeproTech, Inc.). Cells were incubated at 37° C. with 5% $CO_2$. On culture day 2, cells were gently washed and the media was replaced with fresh RPMI-10 containing the same concentrations of GM-CSF and IL-4, and the culture was continued for another 5 days. Dendritic cells were matured by the addition of either 10 μg/ml lipopolysaccharide (LPS; Difco®) or 50 μmol/ml CpG (Mayo Molecular Core Facility) to the cultures for 48 hours. Maturation status was confirmed by staining for Class-11, CD80, and CD86.

Human dendritic cells were derived from monocytes cultured with GM-CSF and IL-4. Day 7 cells were activated with either LPS (10 μg/ml), tumor necrosis factor-α /interleukin-1β (TNF-α/IL-1β; $1.1 \times 10^4$ U/ml and $3.2 \times 10^3$ U/ml, respectively), interferon-γ (IFN-γ; $2 \times 10^3$ U/ml), or PBS control for 3 days. Dendritic cell development was followed by monitoring the presence of the CD83 cell surface marker, as described below.

Flow cytometry—Cells were washed with fluorescence activated cell sorting (FACS) buffer (0.5% bovine serum albumin (BSA) and 0.1% sodium azide in PBS) and centrifuged into a 96-well plate (Nunc). Antibodies were added to the wells for a 30 minute incubation on ice. After three washes with FACS buffer, cells were fixed with 1% paraformaldehyde and analyzed on a FACS Calibur (Becton Dickinson). Data were analyzed using Cell Quest software (BD PharMingen).

Activated human dendritic cells were stained with 10 μg/ml of sHIgM12 or polyclonal hIgM control on culture day 10 (3 days after induction of maturation). FITC-conjugated anti-hIgM secondary antibody was added after several washes. CD83 is a maturation marker on dendritic cells, and was assessed by anti-human CD83-PE antibody.

Human TP365 glioma cells were obtained from Dr. Robert Jenkins at the Mayo Clinic (Rochester, Minn.). Cells were stained with 10 μg/ml sHIgM12 or polyclonal hIgM control. A secondary anti-human IgM, $Fc_{5\mu}$, fragment specific FITC-conjugated antibody (Jackson Immunoresearch Laboratories) was added after 2 washes. Cells subsequently were washed and fixed with 2% paraformaldehyde, and subjected to flow cytometry analysis.

Isolation of endogenous dendritic cells—Dendritic cells were isolated from mouse spleen and thymus. Tissues were cut into small pieces and incubated in RPMI containing 2 mg/ml collagenase (Sigma-Aldrich), 100 μg/ml DNAse (Sigma-Aldrich), and 2% fetal calf serum (Hyclone) for 20 minutes at 37° C. EDTA (0.031 M) was added for 5 minutes. Erythrocytes were lysed with ACK at 37° C., and the remaining cells were counted and used for flow cytometry.

In vitro activation of naïve T cells—Naïve splenocytes were harvested from mice and plated in triplicate after erythrocyte lysis using ACK buffer. $3 \times 10^5$ responder cells were stimulated in vitro for three days with titrating doses of antigen or antigen-pulsed dendritic cells. The plated cells were pulsed with $^3$H-thymidine during the final 18 hours before they were harvested and $^3$H levels determined.

Adoptive transfer of dendritic cells and T cells—Dendritic cells derived from seven-day bone marrow cultures were pulsed overnight with 1 μmol/ml of the class-I restricted peptide Ser-Ile-Ile-Asn-Phe-Glu-Lys-Leu (SEQ ID NO:1) or the class-II restricted peptide Ile-Ser-Gln-Ala-Val-His-Ala-Ala-His-Ala-Glu-Ile-Asn-Glu (SEQ ID NO:2), or with 1 mg/ml chicken ovalbumin. The control antibody or sHIgM12 was co-incubated with the peptide in the cultures at a concentration of 10 μg/ml. Cells were harvested the next day and washed three times with PBS, and $10^7$ cells per mouse were injected intravenously for in vivo priming of T cells.

For experiments to monitor cell division, OT-1 splenocytes were labeled with 5 μM 5- (and 6-) carboxyfluorescein diaceteate succinimidyl ester (CFSE) for 20 minutes at 37° C. prior to adoptive transfer. Following three washes with PBS, $10^7$ CFSE-labeled splenocytes were intravenously injected into each mouse. Dendritic cells and T cells were administered in separate injections. Spleen cells were harvested 2 or 7 days after adoptive transfer and either analyzed directly by flow cytometry or incubated in culture with various concentrations of ovalbumin for three additional days. Cultures were pulsed with $^3$H-thymidine overnight before harvesting and evaluation for $^3$H incorporation as a measure of T cell activation.

Competition for binding—PD-1.Ig was acquired from Lieping Chen at the Mayo Clinic (Rochester, Minn.). The plasmid encoding PD-1.Ig was originally obtained from Drew Pardoll (Johns Hopkins University, Baltimore, Md.). The plasmid was transformed into CHO cells (ATCC, Manassas, Va.), and PD-1.Ig was isolated from culture supernatants using protein G columns (Pharmacia). Dendritic cells were preincubated with PD-1.Ig for 20 minutes at 4° C. before addition of sHIgM12 and subsequent staining with a fluorescein isothiocyanate- (FITC-) conjugated secondary antibody. For the reverse experiments, cells were preincubated with sHIgM12 before addition of PD-1.Ig. An isotype control antibody was used as a control.

Staining of transfected cells—293-T cells and P815 cells were obtained from ATCC. Cells were transiently transfected with expression plasmids encoding either B7-DC or B7-H1 and stained with sHIgM12, PD-1.Ig, or an isotype control antibody.

Ltk cells (ATCC) were transiently transfected with 2.5 μg of pCDNA3.1 (Invitrogen, Carlsbad, Calif.) or 0.5 μg to 10 μg of pCDNA3.1-hB7.DC expression plasmids. After 48 hours, cells were stained with sHIgM12 or polyclonal hIgM control. FITC-conjugated anti-hIgM secondary antibody was added after several washes.

In vivo assays—To evaluate in vivo effects of sHIgM12 on T cell proliferation, mice were treated with 10 μg of sHIgM12 or polyclonal HIgM control on days −1, 0, and +1, and intravenously injected with 1 mg ovalbumin on day 0. On day 7, splenocytes were isolated and pulsed with concentrations of ovalbumin ranging from 1 ng/ml to 1 mg/ml. After three days of culture in vitro, cells were incubated with 1 μCi of $^3$H-thymidine for 16 hours before harvest and determination of $^3$H incorporation.

The effect of sHIgM12 on a lethal tumor cell challenge was evaluated in C57BL/6J mice, C57BL/6-RAG$^{-/-}$ immunodeficient mice, K⁻D⁻ class I knockout mice, and CD4⁻/⁻ knockout mice. The animals received 10 μg of sHIgM12, polyclonal HIgM control, or PBS intravenously on days −1, 0, and +1. All mice received a subcutaneous injection of $2\times10^4$ B16 melanoma cells in the flank on day 0. The presence of tumors was evaluated starting on day 10. Data were pooled from three separate trials. Categorical data was analyzed using Chi-square distribution (C57BL/6J) or Fischer exact test (C57BL/6-RAG⁻/⁻, CD4⁻/⁻ and K⁻D⁻).

For studies of tumor growth, the width and length of subcutaneous tumors were measured on day 17 (C57BL/6) or day 13 (C57BL/6-RAG⁻/⁻). The product of width and length was used as an estimate of tumor size. Statistical comparisons were made using ANOVA.

To evaluate the persistence of anti-tumor resistance in tumor survivors, C57BL/6 mice that survived otherwise lethal B16 melanoma challenge were rechallenged with $2\times10^4$ tumor cells 30 or more days after the primary challenge. Rechallenge was administered on the opposite flank from the primary challenge. No further antibody treatments were administered. As reference points for comparison, naïve animals were treated with sHIgM12 or polyclonal HIgM control and challenged with the same dose of tumor cells. Developing tumors were measured (width and length) on day 14, and data were analyzed by ANOVA.

Cytokine withdrawal assay—Day 5 dendritic cells were plated on 96-well plates at $2\times10^4$ cells per well. Cells were cultured with sHIgM12, A2B5 control antibody, or media to a final concentration of 10 μg/ml in RPMI10 with 10 μg/ml granulocyte macrophage-colony stimulating factor (GM-CSF) and 1 ng/ml interleukin-4 (IL-4). Alternatively, dendritic cells were contacted with immobilized PD-1.Ig prior to plating and culturing in RPMI-10 with GM-CSF and IL-4. Cells were cultured for 5 days before cytokine withdrawal. For cytokine withdrawal, cells were washed and cultured in RPMI-10 alone. After 1 hour, Alamar Blue (Biosource International, Camarillo, Calif.) was added to a final concentration of 10% (v/v). Readings were taken at 6 hour intervals on a CytoFluor multiplate reader (Series 4000, PerSeptive Biosystems, Framingham, Mass.). The fluorescence plate reader was set to an excitation wavelength of 520 nm and an emission wavelength of 590 nm. Each data point was done in triplicate.

Assessment of dendritic cell migration to lymph nodes—Bone marrow from GFP transgenic mice was used to derive GFP⁺ dendritic cells. In some experiments, the cells were pulsed with a Ser-Ile-Ile-Asn-Phe-Glu-Lys-Leu (SEQ ID NO:1) peptide and then treated with sHIgM12 or an isotype control antibody for 16 hours or over night. Cells were subcutaneously injected into mice, and then isolated from the ipsilateral popliteal and inguinal lymph nodes 48 hours after transfer. Contralateral lymph nodes from both treatment groups served as controls. To measure the number of GFP⁺ dendritic cells that migrated to the lymph nodes, samples were stained with PE-conjugated CD11c antibody and analyzed by flow cytometry.

To assess the effect of these GFP⁺ dendritic cells, splenocytes from OT-1 T cell receptor (TcR) transgenic mice ($3\times10^5$ T cells per well) were co-cultured for 4 days with titrated numbers of cells from the ipsilateral draining lymph nodes of mice treated as described above. Cells were pulsed with 1 mCi of ³H-thymidine per well for the final 16 hours of the incubation, and then harvested for measurement of ³H incorporation. Each group was performed in triplicate.

In related studies, GFP⁺ dendritic cells were mixed with sHIgM12 or control antibody (10 μg/ml) immediately prior to transplantation, and the migration of the cells to lymph nodes was assessed as described above. In another group of studies, the cells were transferred without antibody and the mice received three intravenous tail injections of 10 μg sHIgM12 or HIgM control on days −1, 0, and +1 relative to the transplant. Again, lymph nodes were harvested and analyzed as described above.

IL-12 measurement—Day 7 bone marrow derived dendritic cells were treated with sHIgM12, polyclonal HIgM control, or LPS at a final concentration of 10 μg/ml. Supernatants were collected 96 hours after stimulation and an ELISA (BD PharMingen, San Diego, Calif.) was performed for the active fraction of IL-12. The supernatant tested for each treatment group was pooled from 6 separate wells. Experimental groups were tested in triplicate and at numerous dilutions, with each demonstrating a similar profile.

Example 2

A Monoclonal Human IgM Antibody Binds Mouse Dendritic Cells

Dendritic cells were obtained in culture following incubation of mouse bone marrow cells in media supplemented with GM-CSF and IL-4. Cells from seven day cultures were incubated with purified antibodies isolated from human sera, and stained with fluoresceinated goat anti-human antibody as well as antibodies specific for cell surface molecules typically expressed on dendritic cells. As shown in FIG. 1, the human antibody sHIgM12 bound cells in the cultures that expressed high levels of CD11c, class II, and CD86. Polyclonal human IgM, as well as the other tested monoclonal antibodies from patients with gammopathies or from EBV-transformed cell lines did not appreciably bind the dendritic cell populations.

To determine when the cell surface determinant recognized by the sHIgM12 antibody first appears during the in vitro development of dendritic cells, cultured cells were analyzed by flow cytometry at various times during the culture procedure. The determinant first appeared on day 5, approximately 2 days after the appearance of cells expressing high levels of the dendritic cell marker CD11c. The determinant was expressed at even higher levels in cells cultured in the presence of LPS and CpG, two molecular signals associated with bacterial infection.

Dendritic cells isolated from various tissues were examined to establish whether endogenous cells express the determinant bound by sHIgM12 antibody. Dendritic cells freshly isolated from spleen, thymus, and bone marrow all were stained by the sHIgM12 antibody. In contrast, most other bone marrow cells, splenic B cells, splenic T cells, and splenic macrophages were not appreciably stained by sHIgM12. B cells, T cells, NK cells, and macrophages were activated with LPS or concanavalin A to assess whether activated lymphoid or monocytic cells express the antigen. None of the activated cells from these lineages bound sHIgM12. The sHIgM12 antibody therefore appears to bind a cell surface molecule expressed selectively by dendritic cells, and this determinant is expressed increasingly as the dendritic cells mature and become activated.

Example 3

The sHIgM12 Antibody Potentiates Dendritic Antigen-Presenting function

To determine whether binding of sHIgM12 to the surface of dendritic cells influences the pattern of expressed cell surface molecules, day 7 dendritic cell cultures were supplemented with 10 µg/ml antibody, incubated overnight, and analyzed by flow cytometry. No changes in cell surface markers specific to sHIgM12 treatment were observed as compared to cultures treated with human polyclonal IgM antibodies or other monoclonal human IgM antibodies.

Figure 2:
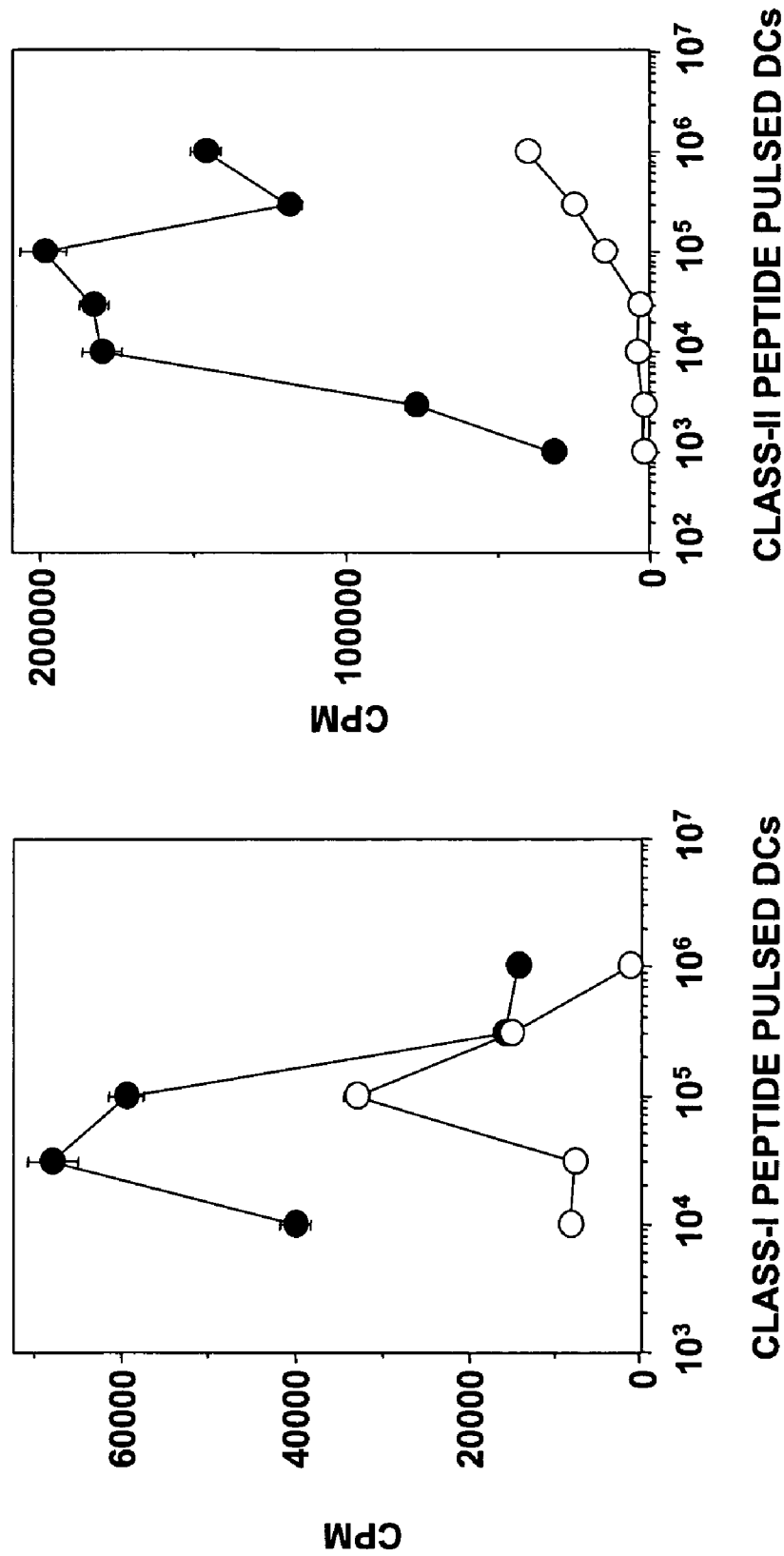
FIG. 2 shows are line graphs showing the effect of sHIgM12-treated, antigen-pulsed dendritic cells on incorporation of $^3$H-thymidine into T cells, an indicator of proliferation. The lop graph shows the MHC class I-restricted T cell response to dendritic cells treated with sHIgM12 (filled circles) or control polyclonal human IgM control (HIgM; open circles). The bottom graph shows the MHC class II-restricted T cell response to dendritic cells treated with sHIgM12 (filled circles) or control polyclonal HIgM (open circles).

The antigen-presenting functions of the dendritic cells were assessed in vitro. Antibody-treated dendritic cells were pulsed with peptide antigen and used to stimulate naïve antigen-specific T cells freshly isolated from OT-1 and DO-11 transgenic mice. T cell activation was measured by incorporation of $^3$H-thymidine as described in Example 1. Dendritic cells that were pulsed with a class I-binding peptide (Ser-Ile-Ile-Asn-Phe-Glu-Lys-Leu; SEQ ID NO:1) and incubated with polyclonal HIgM control antibody were able to activate naïve CD8 T cells from OT-1 mice. Dendritic cells treated with the same peptide and incubated with the monoclonal sHIgM12 antibody activated naïve T cells approximately 10-fold more effectively, as judged by the number of antigen-pulsed dendritic cells required to induce the incorporation of $^3$H-thymidine (FIG. 2A). BALB/c dendritic cells pulsed with a peptide (Ile-Ser-Gln-Ala-Val-His-Ala-Ala-His-Ala-Glu-Ile-Asn-Glu; SEQ ID NO:2) presented by class II molecules were even more effective at activating naïve T cells freshly isolated from DO-11 TcR transgenic mice. Greater than 100-fold more dendritic cells treated with polyclonal HIgM control antibody were needed to activate T cells to levels observed with sHIgM12-treated dendritic cells (FIG. 2B). These experiments demonstrated that the antigen-presenting functions of dendritic cells were dramatically enhanced by treatment of dendritic cells with sHIgM12.

To assess the requirement for direct contact between dendritic cells and T cells in the potentiation of T cell activation, the two cell types are cultured in compartmentalized tissue culture plates that allow soluble factors to move between chambers but do not allow cellular contact between chambers. Alternatively, antibody-depleted supernatants from dendritic cell cultures treated with sHIgM12 are incubated with cultures of transgenic spleen cells or transgenic spleen cells mixed with dendritic cells pulsed with specific antigen.

Figure 3:
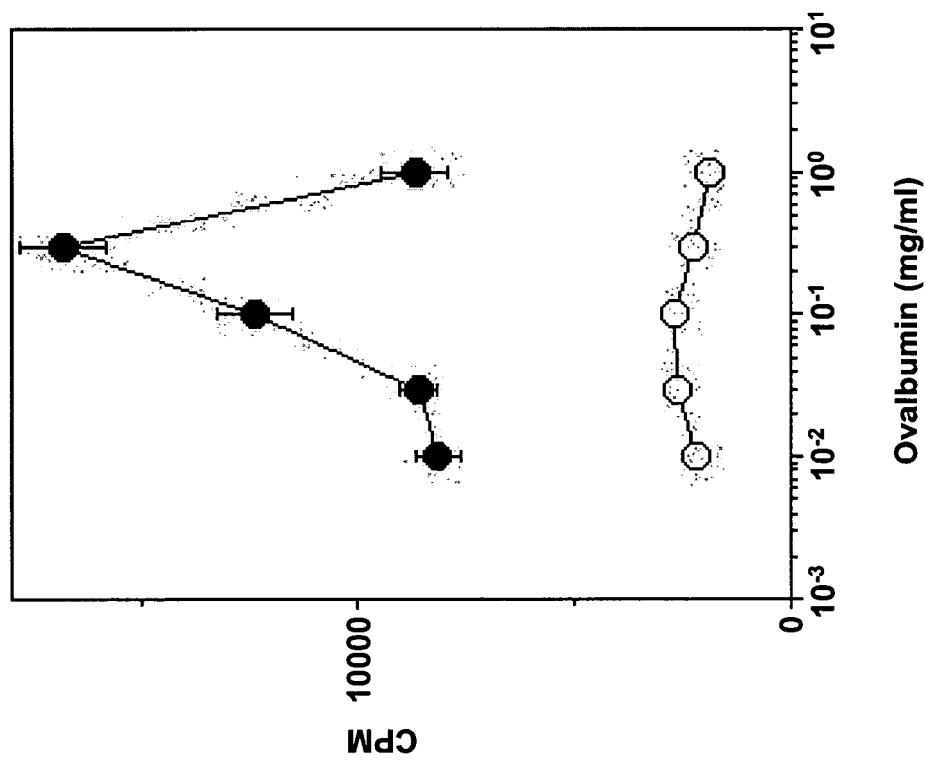
FIG. 3 is a line graph showing the effect of sHIgM12 treated, antigen-pulsed dendritic cells on in vivo T cell priming. Mouse dendritic cells were pulsed with ovalbumin and treated with sHIgM12 (open circles) or polyclonal HIgM control (closed circles) prior to adoptive transfer. The data depict levels of 3H incorporation into splenocytes that were harvested 7 days after adoptive transfer and treated with titrating doses of ovalbumin.

The ability of antigen-pulsed, antibody-treated dendritic cells prepared in vitro to stimulate splenic T cells in vivo was evaluated in C3H/H3J mice. This inbred strain is genetically defective at the TLR-4 locus and consequently is not responsive to LPS, an activator of dendritic cells. Day 7 cultures of mouse bone marrow-derived dendritic cells were incubated overnight with chicken ovalbumin and sHIgM12 or polyclonal HIgM control antibody, and $10^7$ cells were intravenously infused into each mouse. After seven days, spleen cells were removed from the animals, incubated in vitro with various amounts of ovalbumin for three days, and T cell activation was measured by incorporation of $^3$H-thymidine. As shown in FIG. 3, spleen cells from animals that had received sHIgM12-treated dendritic cells responded much more vigorously to secondary challenge with ovalbumin than did spleen cells from mice that received dendritic cells treated with polyclonal HIgM control. Dendritic cells treated in culture with sHIgM12 therefore displayed enhanced ability to stimulate T cells in vivo. Because dendritic cells from the TLR-4 deficient mice were responsive to sHIgM12 treatment, possible contamination by LPS was not a factor in these experiments. In parallel studies, polymixin B was added to the dendritic cell cultures to inactivate potential LPS contaminants. Polymixin B had no influence on dendritic cell function following treatment with sHIgM12, although it was effective in reducing maturation of the dendritic cells when LPS was added directly to the cultures.

To visualize what was happening to the T cells in vivo, C57BL/6 antigen-pulsed, antibody-treated dendritic cells were adoptively transferred along with transgenic OT-1 cells into C57BL/6 hosts. OT-1 T cells were identified in these experiments by probing with $K^b$:Ser-Ile-Ile-Asn-Phe-Glu-Lys-Leu (SEQ ID NO:1) tetramers. Spleen cells were recovered 2 or 7 days after transfer, and tetramer-positive T cells were analyzed by flow cytometry to determine their activation state. T cells stimulated in vivo by dendritic cells pretreated with sHIgM12 expressed substantially higher levels of the activation markers CD44 and CD69 two days after transfer as compared to T cells stimulated by dendritic cells pretreated with PBS. By day 7, cells remaining in the spleen were less activated, but cells transferred into mice receiving sHIgM12-treated dendritic cells still expressed higher levels of CD44 and CD69. Dendritic cells not treated with antigen had no effect on the activation of transgenic T cells upon adoptive transfer, whether pretreated with sHIgM12 or not. Treatment with sHIgM12 therefore potentiated the ability of dendritic cells to activate T cells in vivo.

Example 4

The Pentameric Structure of sHIgM12 Facilitates Potentiation of Dendritic Cells

Figures 4A, 4B:
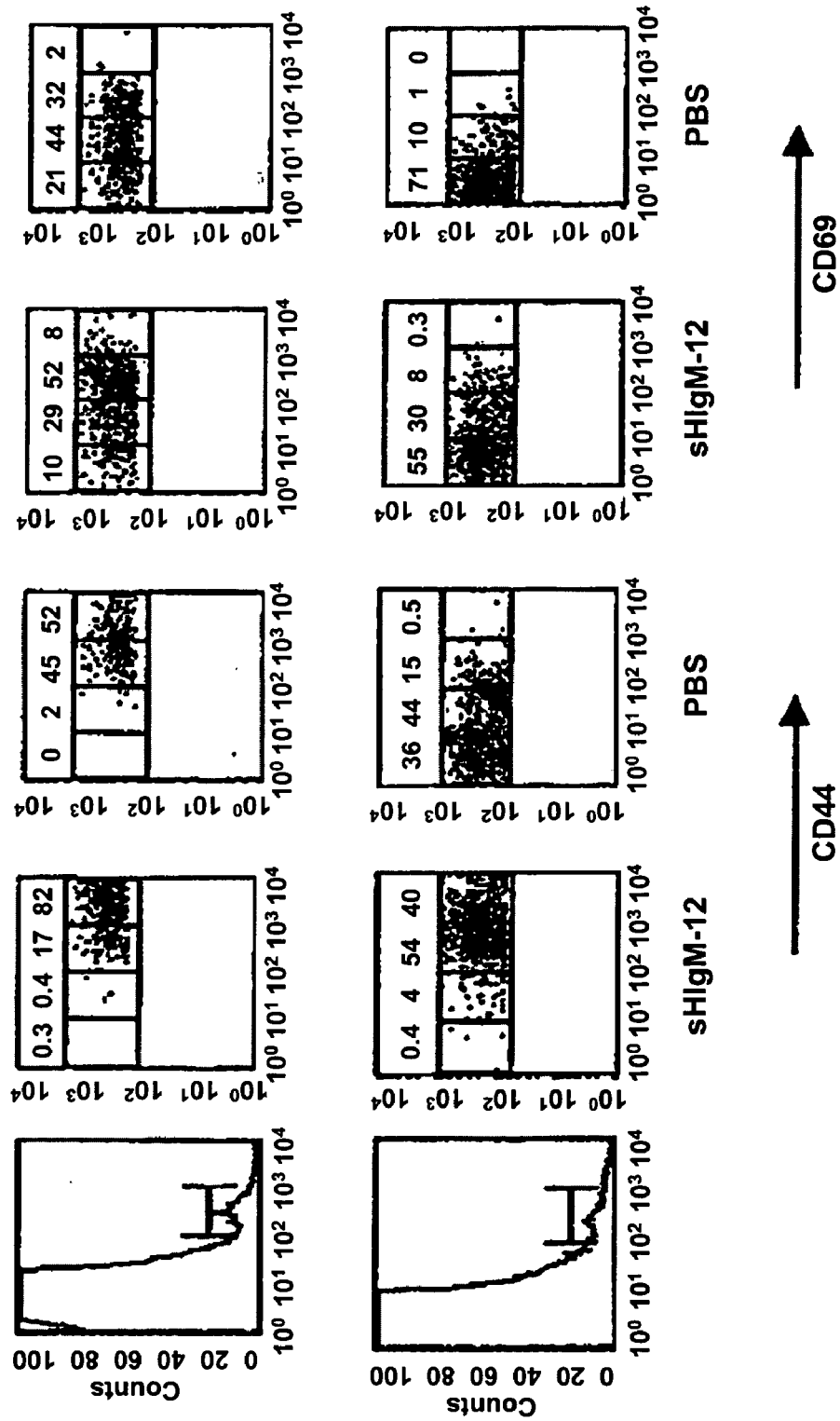
FIG. 4A is a histogram showing amounts of dendritic cell staining by sHIgM12 (gray filled histogram), polyclonal HIgM control (black filled histogram), and monomeric sHIgM12 (thick black line outlining unfilled histogram).
FIG. 4B is a line graph showing levels of activation of naïve OT-1 splenocytes by dendritic cells treated with pentameric sHIgM12 (filled circles), polyclonal HIgM control (open circles), monomeric sHIgM12 (open squares), and monomeric sHIgM12 followed by pentameric sHIgM12 (open triangles).
Figure 5B:
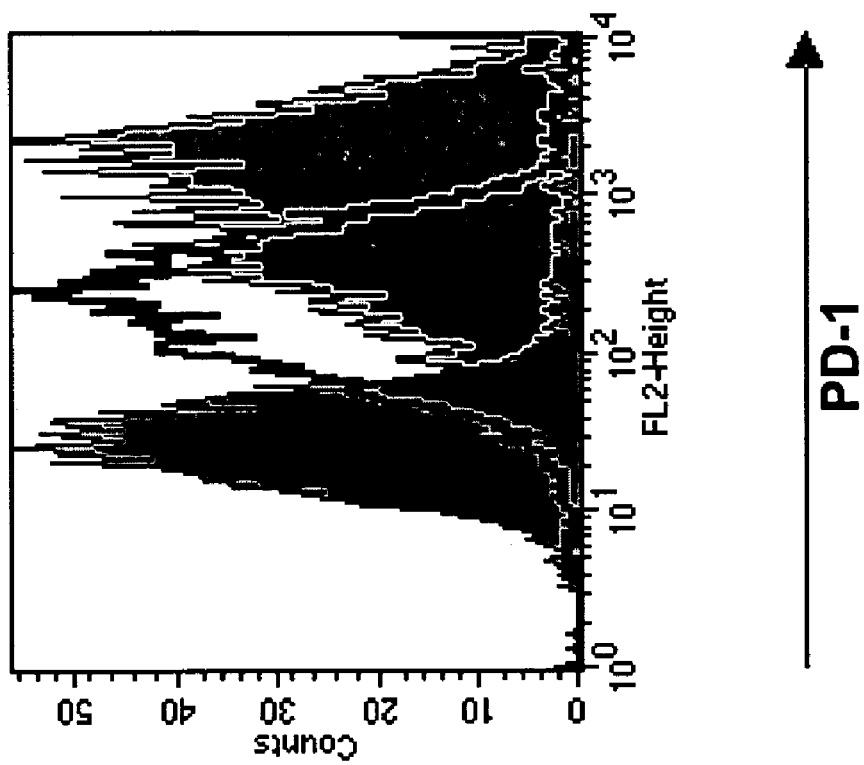
FIG. 5B is a histogram of the reciprocal experiment, showing PD-1.Ig staining of dendritic cells (gray histogram) or dendritic cells preincubated with sHIgM12 (unshaded histogram).
Figure 5A:
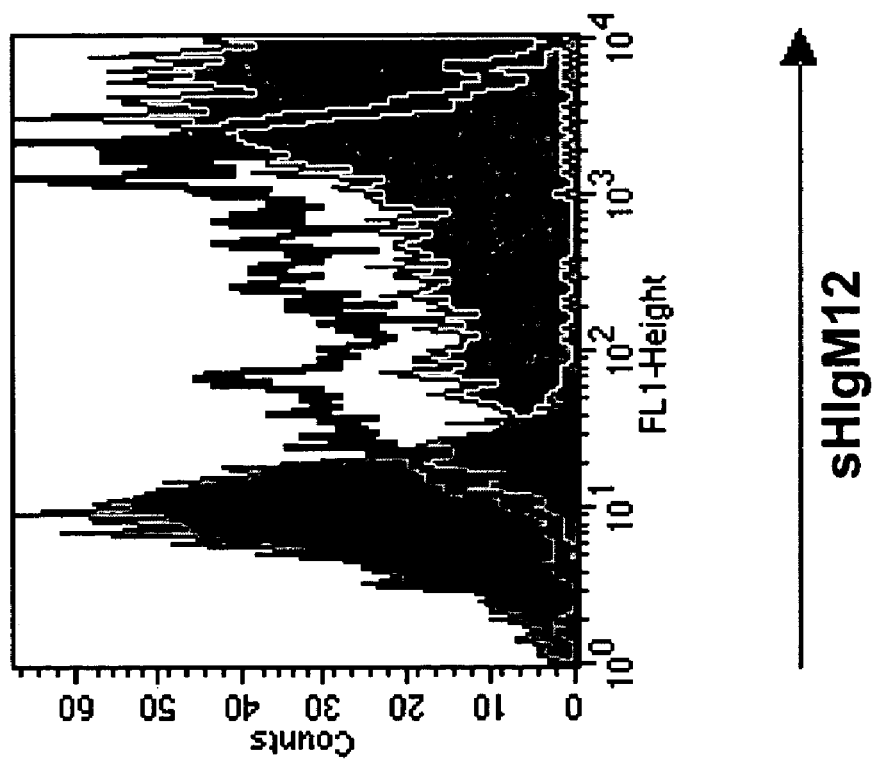
FIG. 5A is a histogram showing levels of sHIgM12 staining of dendritic cells (gray histogram) or dendritic cells preincubated with PK-1.Ig (unshaded histogram). A control antibody (black histogram) did not stain the cells.

To test the hypothesis that low affinity IgM antibodies have the ability to activate cells because they cross-link multiple receptors on the cells surface of targeted cells, monomeric fragments of sHIgM12 were evaluated for their ability to stain dendritic cells, potentiate dendritic cell function, and block the ability of an intact sHIgM12 antibody to potentiate function. IgM monomers were significantly less effective than intact sHIgM12 at staining dendritic cells (FIG. 4A). However, the fragments did stain the cells more than polyclonal IgM antibodies, suggesting that they have intact, low affinity binding sites. Moreover, the antibody fragments were able to block the ability of intact IgM to potentiate dendritic cell antigen-presenting function (FIG. 4B). Overnight treatment with sHIgM12 monomers did not, however, potentiate the ability of dendritic cells to induce T cells to incorporate $^3$H-thymidine. The sHIgM12 antibody therefore may function by cross-linking multiple determinants on dendritic cells. The monomeric fragments can bind the determinants and thus block the ability of the pentamers to cross-link the relevant cell surface structures.

Example 5

B7-DC is the Cognate Receptor for sHIgM12 on Murine Dendritic Cells

To determine the identity of the receptor for sHIgM12 on the surface of dendritic cells, murine bone marrow derived dendritic cells were incubated with or without a soluble PD-1.Ig fusion protein and stained with sHIgM12. Binding of the PD-1 fusion protein attenuated sHIgM12 staining to approximately 50% of the level observed in the absence of PD-1 (FIG. 5A). The reciprocal experiment showed that sHIgM12 also reduced the binding of PD-1 to dendritic cells to about 20% of the level observed in the absence of sHIgM12 (FIG. 5B). The higher avidity of the pentameric IgM antibody may contribute to the higher degree of competition by sHIgM12.

To investigate whether sHIgM12 can bind to B7-DC, 293T cells were transfected with a plasmid encoding murine B7-DC. $2 \times 10^5$ cells were plated and incubated overnight prior to transfection. 2 μg of the expression plasmid was mixed with 5 μl of FU-GENE (Roche) and incubated for 20 minutes in a 37° C. incubator. The mixture was pipetted directly onto the cells. The cells were cultured for 48 hours at 37° C., and then stained with either sHIgM12 or a control antibody. Flow cytometry revealed that approximately 97% of the transfected cells were stained by sHIgM12. Since the PD-1 receptor has been shown to have dual specificity for B7-DC and B7-H1, P815 cells were transfected with B7-H1 to determine whether the epitope for sHIgM12 is conserved between the two family members. sHIgM12 did not bind to P815 cells expressing B7-H1, indicating that the binding to B7-DC is specific.

Example 6

Figure 6:
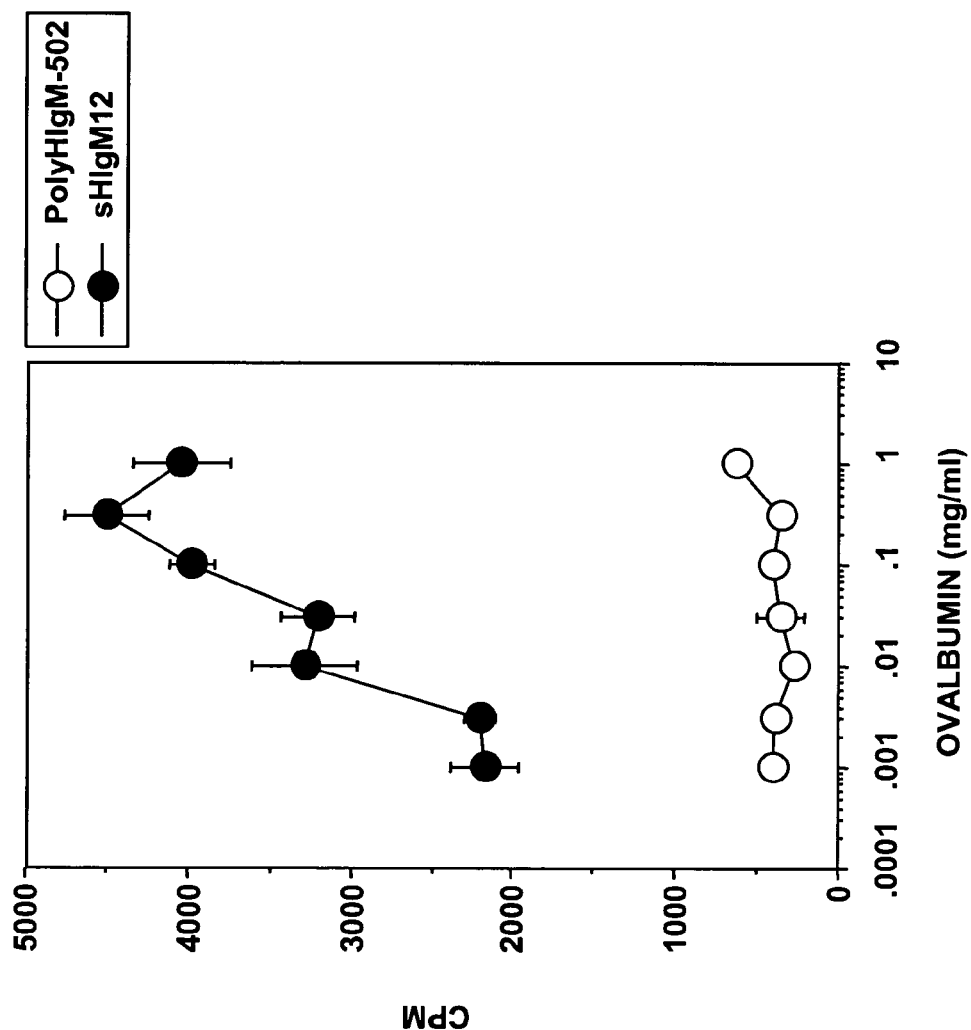
FIG. 6 is a line graph showing the immune response of splenocytes from mice that were treated in vivo with sHIgM12 (filled circles) or polyclonal HIgM control (open circles) before being isolated and immunized with ovalbumin.

Targeting B7-DC on Dendritic Cells Mediates Potentiation of Immune Responses to Protein Antigens and Tumors The systemic effect of sHIgM12 binding to dendritic cells was examined in vivo. Mice were treated with 10 μg sHIgM12 antibody or polyclonal HIgM control on days −1, 0, and +1, and immunized with 1 mg of ovalbumin on day 0. Seven days after immunization, splenocytes were isolated and assayed for a proliferative response against ovalbumin antigens. Splenocytes treated with polyclonal HIgM control did not mount an immune response against ovalbumin. Treatment with sHIgM12, however, led to high levels of proliferation in response to titrated amounts of antigen (FIG. 6). These data indicate that systemic sHIgM12 has profound immune potentiating effects, presumably through its interaction with dendritic cells.

The functional role of sHIgM12 cross-linking of B7-DC was examined in a host immune response against a weakly immunogenic tumor. B 16 melanoma is an aggressive, C57BL/6-derived tumor that is known to kill over 95% of immunocompetent mice inoculated subcutaneously with as few as $2 \times 10^4$ cells. In this model, palpable tumors typically develop 10 to 12 days after inoculation and progress to surface areas in excess of 225 mm$^2$ by day 17. Mice were treated with sHIgM12, polyclonal HIgM control antibody, or PBS injected intravenously on day −1, 0, and +1. All mice received $2 \times 10^4$ B 16 melanoma cells subcutaneously on day 0. Eleven of 16 animals (69%) treated with sHIgM12 remained free from tumors on day 17, whereas only 1 of 13 animals (7%) treated with polyclonal HIgM control was tumor free (p<0.001, Table 1). There was no significant difference in tumor incidence in animals receiving polyclonal HIgM control or PBS. Furthermore, tumor growth was significantly inhibited by sHIgM12 treatment as compared to treatment with IgM control or PBS (p=0.032, Table 2). The delay in growth was transient, as tumors that developed in sHIgM12-treated mice eventually progressed to 225 mm$^2$ in size. Some murine tumor cell lines, particularly those of hematopoietic origin, have been reported to express B7-DC mRNA. The possibility that sHIgM12 may act by directly binding to B7-DC on B 16 melanoma cells, however, was ruled out because flow cytometry experiments indicated the antibody did not appreciably stain tumor cells.

TABLE 1

SHIgM12 treatment protects C57BL/6 mice from lethal challenge with B16 melanoma

| Strain | Treatment | Tumor free (day 17) |
|---|---|---|
| C57BL/6J | Polyclonal HIgM control | 1/13 |
|  | PBS | 0/13* |
|  | sHIgM12 | 11/16** |
| C57BL/6J-RAG$^{-/-}$ | Polyclonal HIgM control | 0/5 |
|  | sHIgM12 | 0/5* |
| K$^-$D$^-$ | Polyclonal HIgM control | 0/5 |
|  | sHIgM12 | 0/5* |
| CD4$^{-/-}$ | Polyclonal HIgM control | 0/9 |
|  | sHIgM12 | 0/9* |

*no statistical difference; ** p < 0.001

To explore the possibility that host resistance to the lethal tumor challenge is immune mediated, the same antibody regimen was used in immunodeficient C57BL/6-RAG$^{-/-}$ mice. Treatment with sHIgM12 had no effect on the appearance or growth of B16 melanoma in these animals (Tables 1 and 2). The role of CD8 T cells in the host immune response to the tumors was established using MHC class I knock-out mice (K$^-$D$^-$). Though these animals have an intact CD4 T cell repertoire, the deficiency in CD8 T cells abolished the protective effect of sHIgM12. Likewise, the absence of a helper response in CD4 knockout mice abrogated the protective effect of sHIgM12 as all of these mice developed palpable tumors akin to mice receiving control treatment. The B-cell immune response as measured by serum levels of anti-tumors antibodies was quantitatively indistinguishable between mice receiving sHIgM12 or polyclonal HIgM control. Mice deficient in class II, immunoglobulin, interferon-γ, tumor necrosis factor, perforin, Fas/FasL, and CD40 also are useful for these studies. Such animals are obtained from The Jackson Laboratory.

TABLE 2 sHIgM12 treatment inhibits tumor growth in immunocompetent C57BL/6 mice

| Strain | Number | Treatment | Avg. tumor size | SEM | Statistics |
|---|---|---|---|---|---|
| C57BL/6 | 13 | Polyclonal HIgM | 163 mm$^2$ | ±21.2 |  |
|  | 7 | PBS | 190 mm$^2$ | ±22.5 | P = 0.666 |
|  | 4 | sHIgM12 | 58 mm$^2$ | ±15.0 | P = 0.032 |
| C57BL/6-RAG$^{-/-}$ | 5 | Polyclonal HIgM | 150 mm$^2$ | ±22.2 |  |
|  | 5 | sHIgM12 | 194 mm$^2$ | ±14.8 | P = 0.138 |

The hallmark of an effective adaptive immune response is a vigorous memory response upon secondary challenge. To determine whether an anamnestic response against B16 tumor antigens was established following treatment with sHIgM12, the surviving mice were re-challenged with a lethal dose of B16 melanoma cells. As shown in Table 3, mice that had survived for 30 days following the initial tumor challenge displayed significant resistance to a secondary challenge (p=0.005). A separate group of mice was re-challenged after surviving for 90 days after the initial tumor cell inoculation. In this study, 100% (4/4) mice remained tumor-free for an additional 30 days following re-challenge. As none of the surviving mice received additional treatment with sHIgM12, the resistance to secondary challenge suggests that an effective anti-tumor immune response was established by treatment with sHIgM12 following the initial challenge. These data indicate an important role for B7-DC in the initial priming and subsequent maintenance of a T cell response to tumor antigens. In addition to B16 melanoma, weakly antigenic sarcomas such as Ag104 and MCA102 also are useful for tumor challenge studies of antibodies such as sHIgM12.

TABLE 3 sHIgM12 treated tumor graft survivors display persistent anti-tumor resistance

| Strain | Number | Treatment | Avg. tumor size | SEM |
|---|---|---|---|---|
| C57BL/6 | 5 | Naïve, polyclonal HIgM | 206 mm$^2$ | ±25.2 |
| | 5 | Naïve, sHIgM12 | 13.6 mm$^{2*}$ | ±13.6 |
| | 5 | Tumor survivor, no additional Ab | 35.6 mm$^{2*}$ | ±20.2 |

*p < 0.001

Enhancement of dendritic cell vaccine therapy using sHIgM12—Since sHIgM12 significantly enhanced T cell activation at the time of adoptive transfer into immunocompetent mice (Example 3), it is possible that sHIgM12 treatment could enhance the protective effect of adoptively transferred dendritic cells primed with antigenic tumor-derived peptides. To test this possibility, syngeneic dendritic cells pulsed with the B 16-derived antigenic peptide Trp2$_{180-188}$ are adoptively transferred into C57BL/6 mice on the earliest day after tumor inoculation on which antibody treatment alone does not protect the mice. Groups of C57BL/6 mice receive dendritic cells pulsed with either tumor specific antigenic peptide or an irrelevant peptide along with sHIgM12 or polyclonal HIgM control. Alternatively, a B16 melanoma variant that expresses chicken ovalbumin is used as an antigen. T cells from OT-1 TcR transgenic mice are adoptively transferred into mice bearing established tumors at various stages (e.g., days +3, +5, +7, +9, and +11) after tumor challenge. The activation, tumor infiltration, and anti-tumor cytotoxicity of T cells bearing the OT-1 receptor are monitored as animals are treated with sHIgM12 or polyclonal HIgM control. OT-1 cells specific for the surrogate tumor antigen are visualized and isolated using T cell-specific class I tetramers such as those generated in response to the antigenic Ser-Ile-Ile-Asn-Phe-Glu-Lys-Leu (SEQ ID NO:1) ovalbumin peptide.

Example 7 sHIgM12 Binding to B7-DC Directly Induces Functional Changes in Dendritic Cells

To examine whether binding of sHIgM12 to B7-DC directly affects dendritic cells biology, dendritic cells were treated in vitro with sHIgM12, polyclonal HIgM control, or LPS. The cells then were analyzed for their ability to (1) survive in culture following cytokine deprivation, (2) migrate to draining lymph nodes following adoptive transfer into naïve animals, and (3) secrete IL-12, a key immunomodulator.

Prolonged survival of dendritic cells could lead to more effective interaction with T cells and thus potentiate immune responses. The possibility that sHIgM12 provides a survival signal to dendritic cells that would otherwise undergo apoptosis was investigated by cytokine withdrawal assays. Murine bone marrow-derived dendritic cells were plated on day 5 into 96-well plates. Cells were cultured with sHIgM12, A2B5 (a control antibody that binds dendritic cells), or media in RPMI-10 containing GM-CSF and IL-4. To achieve cytokines withdrawal, cells were washed in cultured in RPMI-10 alone. Alamar Blue was added one hour after withdrawal. The metabolism of Alamar Blue was measured at 6 hour intervals. The data represent the percentage of cellular metabolism that was maintained 24 hours after cytokine withdrawal, whereby 100% represents the level of metabolism when dendritic cells were cultured with GM-CSF and IL-4, and 0% arbitrarily represents complete cytokine withdrawal.

As shown in FIG. 7A, withdrawal of GM-CSF/IL-4 reduced metabolism to 29% of the level observed in cells cultured in cytokine-supplemented media. Incubating the cells with sHIgM12, however, resulted in 80% maintenance of metabolism levels 24 hours after cytokine withdrawal. Treatment with A2B5 did not significantly improve metabolism in the cultures as compared to treatment with media alone (33% vs. 29%). Additionally, treatment with sHIgM12 resulted in larger numbers of viable, Annexin-V negative dendritic cells 24 hours after cytokine withdrawal than were found in comparable cultures treated with control antibodies. In analogous experiments, dendritic cells were incubated with a PD-1.Ig fusion protein that was immobilized by binding to plastic plates. Treatment with the PD-1.Ig fusion maintained dendritic cell metabolism upon GM-CSF/IL-4 withdrawal in a manner comparable to treatment with sHIgM12 (FIG. 7B), and there was no statistical difference between the two groups. Cells contacted with PD-1.Ig maintained metabolism at statistically higher levels than cells treated with polyclonal HIgM control antibody or PBS (p<0.05). Other IgM antibodies known to bind to dendritic cell membranes also are useful for cytokine withdrawal experiments as described herein. Such antibodies include, for example, the anti-MHC class-I antibodies 28-14-8 (specific for $D^b$) and 28-13-3 (specific for $K^b$), as well as the murine oligodendrocyte-binding antibody 94.03.

The anti-apoptotic activity induced by sHIgM12 indicated that the antibody may induce intracellular signals that inhibit programmed cell death. To evaluate this possibility, bone marrow cells were cultured with GM-CSF and IL-4 for 7 days. Cells were treated with sHIgM12, polyclonal HIgM control, or LPS for various lengths of time, stained with an antibody against the p65 subunit of NFκB, and subsequently stained with an antibody against the dendritic cell marker CD11c. These experiments revealed that NFκB was upregulated between 15 and 30 minutes after addition of sHIgM12. The polyclonal HIgM control had no effect on NFκB levels. The effect of sHIgM12 was specific and was not due to LPS contamination, as dendritic cells from Toll-4 deficient mice did not respond to LPS treatment but did upregulate NFκB after treatment with sHIgM12. The sHIgM12 antibody therefore may bind to dendritic cells and induce intracellular signals that block programmed cell death, thus enhancing the ability of the cells to induce T cell responses against specific antigens.

To further examine whether binding of sHIgM12 to B7-CD has a direct effect on dendritic cell biology and viability, bone marrow-derived dendritic cells from mice transgenic for green fluorescent protein (GFP) were treated in vitro prior to adoptive transfer into syngeneic, non-C57BL/6 transgenic mice. Five-fold more GFP$^+$, CD11c$^+$ dendritic cells were recovered from draining popliteal and inguinal lymph nodes in mice receiving sHIgM12-treated dendritic cells than those receiving cells treated with polyclonal HIgM control. The capacity of lymph node immigrants to potentiate an immune response was tested by concomitant treatment of the dendritic cells with sHIgM12 and Ser-Ile-Ile-Asn-Phe-Glu-Lys-Leu (SEQ ID NO:1) peptide prior to adoptive transfer. In vitro treatment of dendritic cells with anti-B7-DC antibody not only increased the number of dendritic cells recovered by draining lymph nodes, but also increased by 10-fold the ability of these lymph node dendritic cells to induce an antigen-specific T cell response.

The ability of sHIgM12 to modulate dendritic cell function in a distant tissue was tested by mixing the antibody with untreated dendritic cells at the time of transplantation. This experiment was designed to determine whether dendritic cell migration and survival could be enhanced provided that the antibody reaches the transplantation site. Treatment with the sHIgM12 antibody resulted in enhanced dendritic cell migration to draining lymph nodes, while the polyclonal HIgM control did not result in enhanced migration. In related experiments, mice received intravenous doses of sHIgM12 or polyclonal HIgM on the day before, the day of, and the day after dendritic cell transplant. Again, the migration of dendritic cells was increased in the mice that received sHIgM12, while the control did not have such an effect. Systemic administration of the antibody therefore is sufficient to influence dendritic cell biology.

IL-12 is a key factor in promoting Th1-type cellular immunity. Production of IL-12 by dendritic cells treated with sHIgM12 was measured by an ELISA using culture supernatants. Treatment with sHIgM12 stimulated nearly 3-fold higher levels of IL-12 p70 release by dendritic cells than did LPS, a strong danger signal. The polyclonal HIgM control did not elicit detectable levels of IL-12 p70. The increased secretion of IL-12 supports the observation that modulation of B7-DC by sHIgM12 strongly potentiates a cellular immune response against even weakly immunogenic tumors.

Example 8 sHIgM12 Binds to Human Dendritic Cells

To examine whether sHIgM12 also binds the human B7-DC orthologue, human monocyte-derived dendritic cells were stained with sHIgM12 or polyclonal IgM control antibody. sHIgM12 bound weakly to immature dendritic cells. Maturation of the cells with LPS increased the level of sHIgM12 binding, particularly on CD83$^+$ cells. Dendritic cells activated with different stimulation protocols displayed sHIgM12 binding that was increased to varying degrees: cells activated with LPS were bound by sHIgM12 to a high degree, cells activated with TNF-α and IL-1β were bound by sHIgM12 to an intermediate degree, and cells activated with IFN-γ were bound by sHIgM12 to a lesser degree.

To determine whether human B7-DC is a ligand for sHIgM12, Ltk fibroblast cells were transiently transfected with a human B7-DC expression plasmid and cultured for 48 hours. sHIgM12 bound to the B7-DC transfected cells to a significantly higher level than to mock-transfected cells. Furthermore, the level of sHIgM12 binding to L-cells was positively correlated with the amount of B7-DC plasmid used in the transfection.

B7-DC is expressed in a variety of human and murine tumors. To examine whether sHIgM12 binds to tumor cells, human TP365 glioma cells were incubated with the antibody. These cells were stained by sHIgM12 at a level that was significantly higher than the staining by polyclonal IgM control antibody. Furthermore, PCR was used to generate a B7-DC amplicon with DNA from TP365 cells. The sHIgM12 antibody thus may bind to glioma cells via B7-DC.

Example 9

Production of Recombinant Human IgM Antibodies

Figure 8:
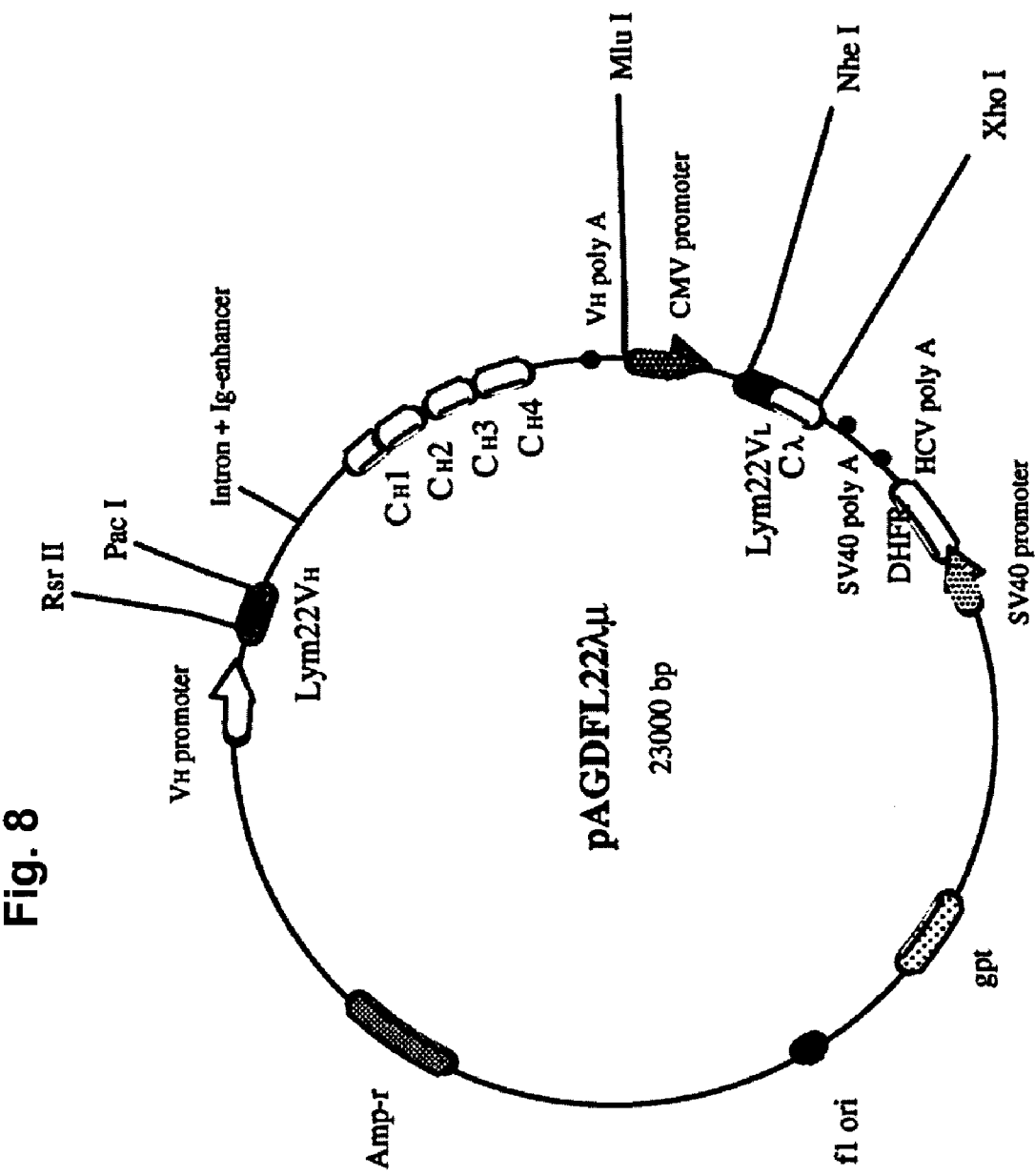
FIG. 8 is a map of an expression vector that can be used to produce antibodies.

Once antibodies of interest such as sHIgM12 are identified, immortalized sources are generated to sustain these important reagents. A vector system has been developed and used to immortalize a human IgM antibody (sHIgM22) identified in the serum of a Waldenstrom's macroglobulinemia patient. The amino acid sequence of the antibody was determined from Fv fragments generated from the serum. Since malignant B cells circulate in the blood of Waldenstrom patients, cDNA encoding the heavy and light chain genes of the antibody present in highest serum concentrations was successfully isolated. These cDNA sequences were used to generate a genomic human IgM heavy chain gene encoding the variable region derived from the patient antibody and a cDNA-based light chain gene expressed under control of the cytomegalovirus (CMV) promoter. These antibody gene sequences were incorporated into a single vector (FIG. 8) along with a selectable dHfR gene expressed under the control of a SV40 promoter. The vector bearing the synthetic antibody genes was introduced into F3B6 hybridoma cells by electroporation. Methotrexate resistant cells were selected and amplified by stepping up the amount of methotrexate in the culture medium. A clone expressing 100 µg antibody per ml of supernatant was recovered. The recombinant antibody displayed all functional properties identified for the antibody isolated from the patient serum.

This same procedure is used to generate a recombinant supply of sHIgM12. An amino acid sequence analysis of sHIgM12 has been performed. Since the amino-terminus of the antibody heavy chain was blocked, Fv fragments were generated to increase the efficiency of obtaining an amino terminal sequence. The amino terminal sequence of the sHIgM12 heavy chain was determined to be Val-Gln-Leu-Gln-Glu-Ser-Gly-Pro-Gly-Leu-L eu-Lys-Pro-Ser-Glu-Thr-Leu-Arg-Ser-Leu-Thr-Asn (SEQ ID NO:3), while the amino terminal sequence of the light chain was determined to be Asp-Ile-Gln-Met-Thr-Gln-Ser-Pro-S er-Ser-Leu-Ser-Ala-Ser-Val-Gly-Asp-Arg-Val (SEQ ID NO:4).

CDNA was isolated from the patient's peripheral blood cells, to be used for recovering full length cDNA copies of the mRNA encoding sHIgM12. In order to ensure than recovered cDNAs truly represent the antibody of interest, the amino acid sequence of CDR3 regions of sHIgM12 are determined. This is accomplished by proteolytic digestion of the Fv fragments and conventional amino acid sequencing of the digestion products. Once the sHIgM12 cDNAs are obtained, they are inserted into a vector which is similar to that described above but has been modified for expression of IgM/Kappa antibodies by substituting the light chain constant region. Recombinant sHIgM12 then is expressed in the human/mouse hybridoma line F3B6 as described above. The modified vector has been used successfully to express the human antibody rHIgM46.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified IgM antibody that binds to B7-DC polypeptides on a cell, wherein said binding results in cross-linking of a plurality of said B7-DC polypeptides, and wherein said IgM. antibody can potentiate an immune response upon administration to a mammal.

2. The purified IgM antibody of claim 1, wherein said cell is a dendritic cell.

3. The purified IgM antibody of claim 1, wherein said cell is a tumor cell.

4. The purified IgM antibody of claim 3, wherein said tumor cell is a glioma tumor cell.

5. The purified IgM antibody of claim 1, wherein said administration is by injection.

6. The purified IgM antibody of claim 1, wherein said mammal is a human.

7. A purified IgM antibody that binds to B7-DC polypeptides on a cell, wherein said binding results in cross-linking of a plurality of said B7-DC polypeptides, and wherein dendritic cells contacted with said molecule exhibit at least one characteristic selected from the group consisting of prolonged longevity, increased NF-κB expression, increased NF-κB translocation to the nucleus, increased ability to activate naive T cells, increased phosphorylation of Akt, increased localization to lymph nodes upon administration to a mammal, maintenance of metabolic rate in culture after cytokine withdrawal, and increased IL-12 secretion.

8. The purified IgM antibody of claim 7, wherein said activation of naive T cells is measured by detection of one or both of CD44 and CD69 on said T cells, or by incorporation of 3H-thymidine into said T cells.

9. A composition comprising the purified IgM antibody of claim 1.

10. The composition of claim 9, further comprising an antigen, wherein said antigen is capable of eliciting an immune response when said composition is administered to a mammal.

11. The composition of claim 10, wherein said antigen is a tumor antigen.

12. The composition of claim 10, wherein said antigen is from a pathogen.

13. The composition of claim 10, wherein said antigen is a component of a killed virus or a component of a killed bacterium.

14. The composition of claim 10, wherein said antigen is a killed virus or a killed bacterium.

15. The composition of claim 10, wherein said mammal is a human.

16. The composition of claim 10, further comprising dendritic cells.

17. An article of manufacture comprising the IgM antibody of claim 1.

18. An article of manufacture comprising the composition of claim 9.

19. The article of manufacture of claim 18, further comprising an antigen, wherein said antigen is capable of eliciting an immune response.

20. The purified IgM antibody of claim 1, wherein said antibody does not display significant binding to other cell surface polypeptides.

21. The purified IgM antibody of claim 7, wherein said antibody does not display significant binding to other cell surface polypeptides.

* * * * *

SEQUENCE LISTING

<160> NUMBER OF SEQ ID NOS: 4

<210> SEQ ID NO 1
<211> LENGTH: 8
<212> TYPE: PRT
<213> ORGANISM: Gallus gallus

<400> SEQUENCE: 1

Ser Ile Ile Asn Phe Glu Lys Leu
 1               5

<210> SEQ ID NO 2
<211> LENGTH: 14
<212> TYPE: PRT
<213> ORGANISM: Gallus gallus

<400> SEQUENCE: 2

Ile Ser Gln Ala Val His Ala Ala His Ala Glu Ile Asn Glu
 1               5                  10

<210> SEQ ID NO 3
<211> LENGTH: 22
<212> TYPE: PRT
<213> ORGANISM: Homo sapiens

<400> SEQUENCE: 3

Val Gln Leu Gln Glu Ser Gly Pro Gly Leu Leu Lys Pro Ser Glu Thr
 1               5                  10                  15

Leu Arg Ser Leu Thr Asn
            20

<210> SEQ ID NO 4
<211> LENGTH: 19
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
 1               5                  10                  15

Asp Arg Val